(12) United States Patent
Bardroff et al.

(10) Patent No.: US 8,715,657 B2
(45) Date of Patent: May 6, 2014

(54) THERAPEUTIC ANTIBODIES BINDING IL12Rβ1

(75) Inventors: Michael Bardroff, Loerrach (DE); Jose M. Carballido Herrera, Allschwil (CH); Daniela Della Ducata, Munich (DE); Christoph Heusser, Oberwil (CH); Ute Jaeger, Munich (DE); Christoph Schwaerzler, St. Louis (FR)

(73) Assignee: Novartis AG, Basel (CH)

( * ) Notice: Subject to any disclaimer, the term of this patent is extended or adjusted under 35 U.S.C. 154(b) by 1 day.

(21) Appl. No.: 13/265,346

(22) PCT Filed: Mar. 29, 2010

(86) PCT No.: PCT/EP2010/054093
§ 371 (c)(1),
(2), (4) Date: Oct. 20, 2011

(87) PCT Pub. No.: WO2010/112458
PCT Pub. Date: Oct. 7, 2010

(65) Prior Publication Data
US 2012/0034231 A1 Feb. 9, 2012

Related U.S. Application Data

(60) Provisional application No. 61/165,177, filed on Apr. 27, 2009.

(51) Int. Cl.
| | |
|---|---|
| *A61K 39/395* | (2006.01) |
| *C07K 16/00* | (2006.01) |
| *C12P 21/08* | (2006.01) |
| *C12P 21/04* | (2006.01) |
| *C12N 15/00* | (2006.01) |
| *C12N 5/02* | (2006.01) |
| *C07H 21/04* | (2006.01) |

(52) U.S. Cl.
USPC .......... 424/130.1; 530/387.1; 530/387.9; 530/388.22; 424/139.1; 424/143.1; 435/69.52; 435/320.1; 435/325; 435/70.1; 536/23.5

(58) Field of Classification Search
None
See application file for complete search history.

(56) References Cited

U.S. PATENT DOCUMENTS

| | | | |
|---|---|---|---|
| 5,853,721 A | 12/1998 | Gately et al. | |
| 6,046,012 A * | 4/2000 | Chizzonite et al. | 435/7.21 |
| 2002/0025317 A1 | 2/2002 | Leung et al. | |
| 2005/0260213 A1* | 11/2005 | Koenig et al. | 424/178.1 |

OTHER PUBLICATIONS

Rudikoff et al., Proc Natl Acad Sci USA 79: 1979-1983, 1982.*
Colman, Research in Immunology 145: 33-36, 1994.*
Kussie et al., J. Immunol. 152: 146-152, 1994.*
Chen et al., EMBO J., 14: 2784-2794, 1995.*
Presky et al., "Analysis of the multiple interactions between IL-12 and the high affinity IL-12 receptor complex," Journal of Immunology 160(5):2174-2179 (Mar. 1, 1998).
Wark et al., "Latest technologies for the enhancement of antibody affinity," Advanced Drug Delievery Reviews 58 (5-6):657-670 (Aug. 7, 2006).
Hoogenboom H.R., "Designing and optimizing library selection strategies for generating high-affinity antibodies," Trends in Biotechnology 15(2):62-70 (Feb. 1, 1997).
Steidl et al., "In vitro affinity maturation of recombinant antibodies by combination of pre-selected CDR-library pools," IP.COM Journal, IP.COM Inc., Oct. 16, 2007.
Hanes et al., "Picomolar Affinity Antibodies from a Fully Synthetic Naive Library Selected and Evolved by Ribosome Display" Nature Biotechnology 18(12):1287-1292 (Dec. 1, 2000).
Presta, L.G., "Engineering Antibodies for Therapy," Current Pharmaceutical Biotechnology 3(3):237-256 (Jan. 1, 2002).
Hezareh et al., "Effector function activities of a panel of mutants of a broadly neutralizing antibody against human immunodeficiency virus type 1," Journal of Virology 75(24): 12161-12168 (Dec. 1, 2001).
Chapman, Andrew, "PEGylated antibodies and antibody fragments for improved therapy: A review" Advanced Drug Delivery Reviews 54(4):531-545 (Jun. 17, 2002).
Altare et al., "Interleukin-12 receptor beta1 deficiency in a patient with abdominal tuberculosis," Journal of Infectious Diseases 184(2):231-236 (Jul. 15, 2001).
Fieschi et al., "A novel form of complete IL-12/IL-23 receptor beta1 deficiency with cell surface-expressed nonfunctional receptors," Blood 104(7):2095-2101 (Oct. 1, 2004).
Lilic et al., "Deregulated production of protective cytokines in response to *Candida albicans* infection in patients with chronic mucocutaneous candidiasis," Infection and Immunity 71(10):5690-5699 (Oct. 2003).
Barrie et al., "The interleukin-12 family of cytokines: Therapeutic targets for inflammatory disease mediation," Clinical and Applied Immunology Reviews 5:225-240 (2005).
Anderson et al., "Interluekin-12 to interleukin 'infinity': the rationale for future therapeutic cytokine targeting," Springer Semin Immun 27:425-442 (2006).

(Continued)

*Primary Examiner* — Christine J Saoud
*Assistant Examiner* — Jegatheesan Seharaseyon
(74) *Attorney, Agent, or Firm* — Karen A. Lacourse

(57) ABSTRACT

The present invention relates to antibodies that specifically bind to IL12Rβ1, the non-signal transducing chain of the heterodimeric IL12 receptor (together with IL12Rβ2 chain) as well as IL23 receptor (together with IL23Rα chain). The invention more specifically relates to specific antibodies that are IL12 and IL23 receptor antagonists capable of inhibiting IL12/IL18 induced IFNγ production of T cells and compositions and methods of use for said antibodies to treat pathological disorders that can be treated by inhibiting IFNγ production, such as rheumatoid arthritis, psoriasis or inflammatory bowel diseases or other autoimmune and inflammatory disorders.

15 Claims, No Drawings

(56) References Cited

OTHER PUBLICATIONS

Ding et al., "ABT-874, a fully human monoclonal anti-IL-12/IL-23 antibody for the potential treatment of autoimmune diseases," Current Opinion in Investigational Drugs 9(5):515-522 (2008).

Vandenbroeck et al., "Inhibiting cytokines of the interleukin-12 family: recent advances and novel challenges," Journal of Pharmacy and Pharmacology 56:145-160 (2004).

Reddy et al., "Modulation of CLA, IL-12R, CD40L, and IL-2Ralpha expression and inhibition of IL-12-and IL-23-induced cytokine secretion by CNTO 1275," Cellular Immunology 247:1-11 (2007).

* cited by examiner

SEQUENCE LISTING

```
<160> NUMBER OF SEQ ID NOS: 41

<210> SEQ ID NO 1
<211> LENGTH: 12
<212> TYPE: PRT
<213> ORGANISM: Artificial
<220> FEATURE:
<223> OTHER INFORMATION: artificial antibody fragment

<400> SEQUENCE: 1

Gly Phe Ser Leu Ser Thr Ser Thr Met Gly Val Ser
1               5                   10

<210> SEQ ID NO 2
<211> LENGTH: 12
<212> TYPE: PRT
<213> ORGANISM: Artificial
<220> FEATURE:
<223> OTHER INFORMATION: artificial antibody fragment

<400> SEQUENCE: 2

Gly Phe Ser Leu Ser Thr Ser Gly Met Gly Val Ser
1               5                   10

<210> SEQ ID NO 3
<211> LENGTH: 10
<212> TYPE: PRT
<213> ORGANISM: Artificial
<220> FEATURE:
<223> OTHER INFORMATION: artificial antibody fragment

<400> SEQUENCE: 3

Gly Phe Thr Phe Ser Ser Tyr Gly Met Ser
1               5                   10

<210> SEQ ID NO 4
<211> LENGTH: 12
<212> TYPE: PRT
<213> ORGANISM: Artificial
<220> FEATURE:
<223> OTHER INFORMATION: artificial antibody fragment

<400> SEQUENCE: 4

Gly Phe Ser Leu Ser Thr Arg Gly Val Gly Val Ser
```

```
<210> SEQ ID NO 5
<211> LENGTH: 16
<212> TYPE: PRT
<213> ORGANISM: Artificial
<220> FEATURE:
<223> OTHER INFORMATION: artificial antibody fragment

<400> SEQUENCE: 5

Trp Ile Tyr Trp Asp Asp Asp Lys Asp Tyr Ser Thr Ser Leu Lys Ser
1               5                   10                  15

<210> SEQ ID NO 6
<211> LENGTH: 16
<212> TYPE: PRT
<213> ORGANISM: Artificial
<220> FEATURE:
<223> OTHER INFORMATION: artificial antibody fragment

<400> SEQUENCE: 6

Leu Ile Asp Trp Thr Asp Asp Lys Tyr Tyr Ser Thr Ser Leu Lys Thr
1               5                   10                  15

<210> SEQ ID NO 7
<211> LENGTH: 19
<212> TYPE: PRT
<213> ORGANISM: Artificial
<220> FEATURE:
<223> OTHER INFORMATION: artificial antibody fragment

<400> SEQUENCE: 7

Tyr Ile Glu Pro Lys Leu Phe Trp Tyr Ala Thr Phe Tyr Ala Ala Ser
1               5                   10                  15

Val Lys Gly

<210> SEQ ID NO 8
<211> LENGTH: 16
<212> TYPE: PRT
<213> ORGANISM: Artificial
<220> FEATURE:
<223> OTHER INFORMATION: artificial antibody fragment

<400> SEQUENCE: 8

Leu Ile Tyr Trp Asp Glu Asp Lys Tyr Tyr Ser Thr Ser Leu Lys Thr
1               5                   10                  15

<210> SEQ ID NO 9
<211> LENGTH: 10
<212> TYPE: PRT
<213> ORGANISM: Artificial
<220> FEATURE:
<223> OTHER INFORMATION: artificial antibody fragment

<400> SEQUENCE: 9

Ala Asn Pro Asp Leu Gly Tyr Phe Asp Tyr
1               5                   10

<210> SEQ ID NO 10
<211> LENGTH: 11
<212> TYPE: PRT
<213> ORGANISM: Artificial
<220> FEATURE:
<223> OTHER INFORMATION: artificial antibody fragment

<400> SEQUENCE: 10

Thr Val Gly Lys Gly Leu Tyr Arg Val Asp Asn
```

<210> SEQ ID NO 11
<211> LENGTH: 11
<212> TYPE: PRT
<213> ORGANISM: Artificial
<220> FEATURE:
<223> OTHER INFORMATION: artificial antibody fragment

<400> SEQUENCE: 11

Asn Asp Phe Met Glu Pro Ala Tyr Phe Ala Leu
1               5                   10

<210> SEQ ID NO 12
<211> LENGTH: 16
<212> TYPE: PRT
<213> ORGANISM: Artificial
<220> FEATURE:
<223> OTHER INFORMATION: artificial antibody fragment

<400> SEQUENCE: 12

Tyr Gln Ser Gly Tyr Tyr Tyr Asn Asn Asp Gly Trp Gly Val Asp Ile
1               5                   10                  15

<210> SEQ ID NO 13
<211> LENGTH: 14
<212> TYPE: PRT
<213> ORGANISM: Artificial
<220> FEATURE:
<223> OTHER INFORMATION: artificial antibody fragment

<400> SEQUENCE: 13

Thr Gly Thr Ser Ser Asp Leu Gly Glu Ser Asn Tyr Val Ser
1               5                   10

<210> SEQ ID NO 14
<211> LENGTH: 11
<212> TYPE: PRT
<213> ORGANISM: Artificial
<220> FEATURE:
<223> OTHER INFORMATION: artificial antibody fragment

<400> SEQUENCE: 14

Ser Gly Asp Asn Leu Gly Ser Lys Phe Ala Tyr
1               5                   10

<210> SEQ ID NO 15
<211> LENGTH: 11
<212> TYPE: PRT
<213> ORGANISM: Artificial
<220> FEATURE:
<223> OTHER INFORMATION: artificial antibody fragment

<400> SEQUENCE: 15

Ser Gly Asp Asn Leu Gly Ser Tyr Tyr Ala Tyr
1               5                   10

<210> SEQ ID NO 16
<211> LENGTH: 11
<212> TYPE: PRT
<213> ORGANISM: Artificial
<220> FEATURE:
<223> OTHER INFORMATION: artificial antibody fragment

<400> SEQUENCE: 16

Arg Ala Ser Gln Ser Ile Ser Ser Trp Leu Asn
1               5                   10

<210> SEQ ID NO 17
<211> LENGTH: 7
<212> TYPE: PRT
<213> ORGANISM: Artificial
<220> FEATURE:
<223> OTHER INFORMATION: artificial antibody fragment

<400> SEQUENCE: 17

Asp Val Asn Lys Arg Pro Ser
1               5

<210> SEQ ID NO 18
<211> LENGTH: 7
<212> TYPE: PRT
<213> ORGANISM: Artificial
<220> FEATURE:
<223> OTHER INFORMATION: artificial antibody fragment

<400> SEQUENCE: 18

Asp Asp Ser Lys Arg Pro Ser
1               5

<210> SEQ ID NO 19
<211> LENGTH: 7
<212> TYPE: PRT
<213> ORGANISM: Artificial
<220> FEATURE:
<223> OTHER INFORMATION: artificial antibody fragment

<400> SEQUENCE: 19

Asp Asp Ser Glu Arg Pro Ser
1               5

<210> SEQ ID NO 20
<211> LENGTH: 7
<212> TYPE: PRT
<213> ORGANISM: Artificial
<220> FEATURE:
<223> OTHER INFORMATION: artificial antibody fragment

<400> SEQUENCE: 20

Ala Ala Ser Ser Leu Gln Ser
1               5

<210> SEQ ID NO 21
<211> LENGTH: 8
<212> TYPE: PRT
<213> ORGANISM: Artificial
<220> FEATURE:
<223> OTHER INFORMATION: artificial antibody fragment

<400> SEQUENCE: 21

Gly Ser Tyr Asp Glu Glu Asp Asn
1               5

<210> SEQ ID NO 22
<211> LENGTH: 10
<212> TYPE: PRT
<213> ORGANISM: Artificial
<220> FEATURE:
<223> OTHER INFORMATION: artificial antibody fragment

<400> SEQUENCE: 22

Gln Ser Trp Asp Ser Ser Ser Gly Asn Asp
1               5                   10

<210> SEQ ID NO 23

```
<211> LENGTH: 9
<212> TYPE: PRT
<213> ORGANISM: Artificial
<220> FEATURE:
<223> OTHER INFORMATION: artificial antibody fragment

<400> SEQUENCE: 23

Ser Ser Tyr Thr Tyr Ser Lys Asn Asn
1               5

<210> SEQ ID NO 24
<211> LENGTH: 8
<212> TYPE: PRT
<213> ORGANISM: Artificial
<220> FEATURE:
<223> OTHER INFORMATION: artificial antibody fragment

<400> SEQUENCE: 24

Gln Gln Tyr Tyr Ala Phe Pro His
1               5

<210> SEQ ID NO 25
<211> LENGTH: 111
<212> TYPE: PRT
<213> ORGANISM: Artificial
<220> FEATURE:
<223> OTHER INFORMATION: artificial antibody fragment

<400> SEQUENCE: 25

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Leu Gly Glu Ser
            20                  25                  30

Asn Tyr Val Ser Trp Tyr Gln Gln His Pro Gly Lys Ala Pro Lys Val
        35                  40                  45

Met Ile Tyr Asp Val Asn Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gly Ser Tyr Asp Glu Glu
                85                  90                  95

Asp Asn Val Phe Gly Gly Gly Thr Lys Leu Thr Val Leu Gly Gln
            100                 105                 110

<210> SEQ ID NO 26
<211> LENGTH: 110
<212> TYPE: PRT
<213> ORGANISM: Artificial
<220> FEATURE:
<223> OTHER INFORMATION: artificial antibody fragment

<400> SEQUENCE: 26

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Lys Phe Ala
            20                  25                  30

Tyr Trp Tyr Gln Gln Lys Pro Gly Gln Ala Pro Val Leu Val Ile Tyr
        35                  40                  45

Asp Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80
```

Asp Glu Ala Asp Tyr Tyr Cys Gln Ser Trp Asp Ser Ser Gly Asn
                85                  90                  95

Asp Val Phe Gly Gly Gly Thr Lys Leu Thr Val Leu Gly Gln
            100                 105                 110

<210> SEQ ID NO 27
<211> LENGTH: 109
<212> TYPE: PRT
<213> ORGANISM: Artificial
<220> FEATURE:
<223> OTHER INFORMATION: artificial antibody fragment

<400> SEQUENCE: 27

Asp Ile Glu Leu Thr Gln Pro Pro Ser Val Ser Val Ala Pro Gly Gln
1               5                   10                  15

Thr Ala Arg Ile Ser Cys Ser Gly Asp Asn Leu Gly Ser Tyr Tyr Ala
            20                  25                  30

Tyr Trp Tyr Gln Gln Lys Pro Gly Gln Ala Pro Val Gly Val Ile Tyr
        35                  40                  45

Asp Asp Ser Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Ser Ser Tyr Thr Tyr Ser Lys Asn Asn
                85                  90                  95

Val Phe Gly Gly Gly Thr Lys Leu Thr Val Leu Gly Gln
            100                 105

<210> SEQ ID NO 28
<211> LENGTH: 109
<212> TYPE: PRT
<213> ORGANISM: Artificial
<220> FEATURE:
<223> OTHER INFORMATION: artificial antibody fragment

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ala Phe Pro His
                85                  90                  95

Thr Phe Gly Gln Gly Thr Lys Val Glu Ile Lys Arg Thr
            100                 105

<210> SEQ ID NO 29
<211> LENGTH: 120
<212> TYPE: PRT
<213> ORGANISM: Artificial
<220> FEATURE:
<223> OTHER INFORMATION: artificial antibody fragment

<400> SEQUENCE: 29

Gln Val Gln Leu Lys Glu Ser Gly Pro Ala Leu Val Lys Pro Thr Gln
1               5                   10                  15

```
Thr Leu Thr Leu Thr Cys Thr Phe Ser Gly Phe Ser Leu Ser Thr Ser
            20                  25                  30

Thr Met Gly Val Ser Trp Ile Arg Gln Pro Pro Gly Lys Ala Leu Glu
        35                  40                  45

Trp Leu Ala Trp Ile Tyr Trp Asp Asp Asp Lys Asp Tyr Ser Thr Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Ala Asn Pro Asp Leu Gly Tyr Phe Asp Tyr Trp Gly Gln
                100                 105                 110

Gly Thr Leu Val Thr Val Ser Ser
            115                 120

<210> SEQ ID NO 30
<211> LENGTH: 121
<212> TYPE: PRT
<213> ORGANISM: Artificial
<220> FEATURE:
<223> OTHER INFORMATION: artificial antibody fragment

<400> SEQUENCE: 30

Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala Leu Ile Asp Trp Thr Asp Asp Lys Tyr Tyr Ser Thr Ser
50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
            85                  90                  95

Cys Ala Arg Thr Val Gly Lys Gly Leu Tyr Arg Val Asp Asn Trp Gly
                100                 105                 110

Gln Gly Thr Leu Val Thr Val Ser Ser
            115                 120

<210> SEQ ID NO 31
<211> LENGTH: 122
<212> TYPE: PRT
<213> ORGANISM: Artificial
<220> FEATURE:
<223> OTHER INFORMATION: artificial antibody fragment

<400> SEQUENCE: 31

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met Ser Trp Val Arg Gln Ala Pro Gly Lys Gly Leu Glu Trp Val
        35                  40                  45

Ser Tyr Ile Glu Pro Lys Leu Phe Trp Tyr Ala Thr Phe Tyr Ala Ala
50                  55                  60

Ser Val Lys Gly Arg Phe Thr Ile Ser Arg Asp Asn Ser Lys Asn Thr
65                  70                  75                  80
```

```
Leu Tyr Leu Gln Met Asn Ser Leu Arg Ala Glu Asp Thr Ala Val Tyr
                85                  90                  95

Tyr Cys Ala Arg Asn Asp Phe Met Glu Pro Ala Tyr Phe Ala Leu Trp
            100                 105                 110

Gly Gln Gly Thr Leu Val Thr Val Ser Ser
        115                 120
```

<210> SEQ ID NO 32
<211> LENGTH: 126
<212> TYPE: PRT
<213> ORGANISM: Artificial
<220> FEATURE:
<223> OTHER INFORMATION: artificial antibody fragment

<400> SEQUENCE: 32

```
Gln Val Gln Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Arg
            20                  25                  30

Gly Val Gly Val Ser Trp Ile Arg Gln Pro Pro Gly Lys Ala Leu Glu
        35                  40                  45

Trp Leu Ala Leu Ile Tyr Trp Asp Glu Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Tyr Gln Ser Gly Tyr Tyr Asn Asn Asp Gly Trp Gly
            100                 105                 110

Val Asp Ile Trp Gly Gln Gly Thr Leu Val Thr Val Ser Ser
        115                 120                 125
```

<210> SEQ ID NO 33
<211> LENGTH: 333
<212> TYPE: DNA
<213> ORGANISM: Artificial
<220> FEATURE:
<223> OTHER INFORMATION: artificial antibody fragment

<400> SEQUENCE: 33

```
gacatcgccc tgacccagcc cgccagcgtg tctggcagcc ctggccagag catcaccatc      60
agctgcaccg gcaccagcag cgacctgggc gagagcaact acgtgtcctg gtatcagcag     120
caccccggca aggccccaa ggtgatgatc tacgacgtga acaagcggcc cagcggcgtg     180
tccaaccggt tcagcggcag caagagcggc aacaccgcca gcctgaccat cagcggactg     240
caggccgagg acgaggccga ctactactgc ggcagctacg acgaagagga caacgtgttt     300
ggcggcggaa caaagcttac cgtcctaggt cag                                  333
```

<210> SEQ ID NO 34
<211> LENGTH: 330
<212> TYPE: DNA
<213> ORGANISM: Artificial
<220> FEATURE:
<223> OTHER INFORMATION: artificial antibody fragment

<400> SEQUENCE: 34

```
gacatcgagc tgacccagcc ccccagcgtg tctgtggccc ctggccagac cgcccggatc      60
agctgcagcg gcgacaacct gggcagcaag ttcgcctact ggtatcagca gaagcccggc     120
```

```
caggcccccg tgctggtgat ctacgacgac agcaagcggc ccagcggcat ccccgagcgg    180
ttcagcggca gcaacagcgg caacaccgcc accctgacca tcagcggcac ccaggccgag    240
gacgaggccg actactactg ccagagctgg acagcagct ccggcaacga cgtgttttggc   300 ggcggaacaa agcttaccgt cctaggtcag                                     330
```

<210> SEQ ID NO 35
<211> LENGTH: 327
<212> TYPE: DNA
<213> ORGANISM: Artificial
<220> FEATURE:
<223> OTHER INFORMATION: artificial antibody fragment

<400> SEQUENCE: 35

```
gacatcgagc tgacccagcc ccccagcgtg tctgtggccc ctggccagac cgcccggatc     60
agctgcagcg gcgacaacct gggcagctac tacgcctact ggtatcagca gaagcccggc    120
caggcccctg tgggcgtgat ctacgacgac agcgagcggc ccagcggcat ccccgagcgg    180
ttcagcggca gcaacagcgg caacaccgcc accctgacca tcagcggcac ccaggccgag    240
gacgaggccg actactactg cagcagctac acctacagca gaacaacgt gtttggcggc     300 ggaacaaagc ttaccgtcct aggtcag                                         327
```

<210> SEQ ID NO 36
<211> LENGTH: 327
<212> TYPE: DNA
<213> ORGANISM: Artificial
<220> FEATURE:
<223> OTHER INFORMATION: artificial antibody fragment

<400> SEQUENCE: 36

```
gatatccaga tgacccagag cccgtctagc ctgagcgcga gcgtgggtga tcgtgtgacc     60
attacctgca gcgagcca gtctatttct tcttggctga attggtacca gcagaaacca    120
ggtaaagcac cgaaactatt aatttatgct gcttcttctt tgcaaagcgg ggtcccgtcc    180
cgttttagcg gctctggatc cggcactgat tttaccctga ccattagcag cctgcaacct    240
gaagactttg cgacctatta ttgccagcag tattatgctt ttcctcatac ctttggccag    300
ggtacgaaag ttgaaattaa acgtacg                                         327
```

<210> SEQ ID NO 37
<211> LENGTH: 360
<212> TYPE: DNA
<213> ORGANISM: Artificial
<220> FEATURE:
<223> OTHER INFORMATION: artificial antibody fragment

<400> SEQUENCE: 37

```
caggtgcagc tgaaagagag cggccctgcc ctggtcaagc ccacccagac cctgaccctg     60
acatgcacct tcagcggctt cagcctgagc accagcacca tgggcgtgtc ctggatccgg    120 cagcccctg gcaaggccct ggaatggctg gcctggatct actgggacga cgacaaggac    180
tacagcacca gcctgaagag ccggctgacc atcagcaagg acaccagcaa gaaccaggtg    240
gtgctgacca tgaccaacat ggaccccgtg gacaccgcca cctactactg cgccagagcc    300
aaccccgacc tgggctactt cgactactgg ggccagggca ccctggtcac cgtctcctca    360
```

<210> SEQ ID NO 38
<211> LENGTH: 363
<212> TYPE: DNA
<213> ORGANISM: Artificial
<220> FEATURE:

<223> OTHER INFORMATION: artificial antibody fragment

<400> SEQUENCE: 38

```
caggtgcagc tgaaagagag cggccctgcc ctggtcaagc ccacccagac cctgaccctg    60
acatgcacct tcagcggctt cagcctgagc accagcggca tgggcgtgtc ctggatccgg   120
cagcccctg  gcaaggccct ggaatggctg gccctgatcg actggaccga cgacaagtac   180
tacagcacca gcctgaaaac ccggctgacc atcagcaagg acaccagcaa gaaccaggtg   240
gtgctgacca tgaccaacat ggaccccgtg gacaccgcca cctactactg cgcccggaca   300
gtgggcaagg gcctgtaccg ggtggacaac tggggccagg gcaccctggt caccgtctcc   360
tca                                                                 363
```

<210> SEQ ID NO 39
<211> LENGTH: 366
<212> TYPE: DNA
<213> ORGANISM: Artificial
<220> FEATURE:
<223> OTHER INFORMATION: artificial antibody fragment

<400> SEQUENCE: 39

```
caggtgcagc tggtcgagag cggcggaggg ctggtgcagc ctggcggcag cctgagactg    60
agctgcgccg ccagcggctt caccttcagc agctacggca tgagctgggt gcggcaggcc   120
cctggcaagg gcctggaatg ggtgtcctac atcgagccca gctgttctg  gtacgccacc   180
ttctacgccg cctccgtgaa gggccggttc accatcagcc gggacaacag caagaacacc   240
ctgtacctgc agatgaacag cctgcgggcc gaggacaccg ccgtgtacta ctgcgcccgg   300
aacgacttca tggaacccgc ctacttcgcc ctgtggggcc agggcaccct ggtcaccgtc   360
tcctca                                                              366
```

<210> SEQ ID NO 40
<211> LENGTH: 378
<212> TYPE: DNA
<213> ORGANISM: Artificial
<220> FEATURE:
<223> OTHER INFORMATION: artificial antibody fragment

<400> SEQUENCE: 40

```
caggtgcaat tgaaagaaag cggcccggcc ctggtgaaac cgacccaaac cctgaccctg    60
acctgtacct tttccggatt tagcctgtct actcgtggtg ttggtgtgtc ttggattcgc   120
cagccgcctg ggaaagccct cgagtggctg gctcttatct attgggatga ggataagtat   180
tatagcacca gcctgaaaac gcgtctgacc attagcaaag atacttcgaa aaatcaggtg   240
gtgctgacta tgaccaacat ggaccgcgtg gatacggcca cctattattg cgcgcgttat   300
cagtctggtt attattataa taatgatggt tggggtgttg atatttgggg ccaaggcacc   360
ctggtgacgg ttagctca                                                 378
```

<210> SEQ ID NO 41
<211> LENGTH: 662
<212> TYPE: PRT
<213> ORGANISM: Homo sapiens

<400> SEQUENCE: 41

```
Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
                20                  25                  30
```

```
Asp Pro Pro Tyr Pro Asp Ala Asp Ser Gly Ser Ala Ser Gly Pro Arg
    35                  40                  45
Asp Leu Arg Cys Tyr Arg Ile Ser Ser Asp Arg Tyr Glu Cys Ser Trp
 50                  55                  60
Gln Tyr Glu Gly Pro Thr Ala Gly Val Ser His Phe Leu Arg Cys Cys
 65                  70                  75                  80
Leu Ser Ser Gly Arg Cys Cys Tyr Phe Ala Ala Gly Ser Ala Thr Arg
                 85                  90                  95
Leu Gln Phe Ser Asp Gln Ala Gly Val Ser Val Leu Tyr Thr Val Thr
                100                 105                 110
Leu Trp Val Glu Ser Trp Ala Arg Asn Gln Thr Glu Lys Ser Pro Glu
            115                 120                 125
Val Thr Leu Gln Leu Tyr Asn Ser Val Lys Tyr Glu Pro Pro Leu Gly
        130                 135                 140
Asp Ile Lys Val Ser Lys Leu Ala Gly Gln Leu Arg Met Glu Trp Glu
145                 150                 155                 160
Thr Pro Asp Asn Gln Val Gly Ala Glu Val Gln Phe Arg His Arg Thr
                165                 170                 175
Pro Ser Ser Pro Trp Lys Leu Gly Asp Cys Gly Pro Gln Asp Asp Asp
            180                 185                 190
Thr Glu Ser Cys Leu Cys Pro Leu Glu Met Asn Val Ala Gln Glu Phe
        195                 200                 205
Gln Leu Arg Arg Arg Gln Leu Gly Ser Gln Gly Ser Ser Trp Ser Lys
    210                 215                 220
Trp Ser Ser Pro Val Cys Val Pro Pro Glu Asn Pro Pro Gln Pro Gln
225                 230                 235                 240
Val Arg Phe Ser Val Glu Gln Leu Gly Gln Asp Gly Arg Arg Arg Leu
                245                 250                 255
Thr Leu Lys Glu Gln Pro Thr Gln Leu Glu Leu Pro Glu Gly Cys Gln
            260                 265                 270
Gly Leu Ala Pro Gly Thr Glu Val Thr Tyr Arg Leu Gln Leu His Met
        275                 280                 285
Leu Ser Cys Pro Cys Lys Ala Lys Ala Thr Arg Thr Leu His Leu Gly
    290                 295                 300
Lys Met Pro Tyr Leu Ser Gly Ala Ala Tyr Asn Val Ala Val Ile Ser
305                 310                 315                 320
Ser Asn Gln Phe Gly Pro Gly Leu Asn Gln Thr Trp His Ile Pro Ala
                325                 330                 335
Asp Thr His Thr Glu Pro Val Ala Leu Asn Ile Ser Val Gly Thr Asn
            340                 345                 350
Gly Thr Thr Met Tyr Trp Pro Ala Arg Ala Gln Ser Met Thr Tyr Cys
        355                 360                 365
Ile Glu Trp Gln Pro Val Gly Gln Asp Gly Gly Leu Ala Thr Cys Ser
    370                 375                 380
Leu Thr Ala Pro Gln Asp Pro Asp Pro Ala Gly Met Ala Thr Tyr Ser
385                 390                 395                 400
Trp Ser Arg Glu Ser Gly Ala Met Gly Gln Glu Lys Cys Tyr Tyr Ile
                405                 410                 415
Thr Ile Phe Ala Ser Ala His Pro Glu Lys Leu Thr Leu Trp Ser Thr
            420                 425                 430
Val Leu Ser Thr Tyr His Phe Gly Gly Asn Ala Ser Ala Ala Gly Thr
        435                 440                 445
Pro His His Val Ser Val Lys Asn His Ser Leu Asp Ser Val Ser Val
    450                 455                 460
```

```
Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
            500                 505                 510

Gly Val Ala Tyr Thr Val Gln Val Arg Ala Asp Thr Ala Trp Leu Arg
        515                 520                 525

Gly Val Trp Ser Gln Pro Gln Arg Phe Ser Ile Glu Val Gln Val Ser
        530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
        610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
            645                 650                 655

Arg Cys Lys Ala Lys Met
            660
```

THERAPEUTIC ANTIBODIES BINDING IL12Rβ1

This application is a U.S. National Phase filing of International Serial No. PCT/EP10/054,093 filed Mar. 29, 2010, and claims priority to U.S. Application Ser. No. 61/165,177 filed Apr. 27, 2009, the contents of which are incorporated herein by reference in their entirety.

The present invention relates to antibodies that specifically bind to IL12Rβ1, the non-signal transducing chain of the heterodimeric IL12 receptor (together with IL12Rβ2 chain) as well as IL23 receptor (together with IL23Rα chain). The invention more specifically relates to specific antibodies that are IL12 and IL23 receptor antagonists capable of inhibiting IL12/IL18 induced IFNγ production of blood cells and compositions and methods of use for said antibodies to treat pathological disorders that can be treated by inhibiting IFNγ production, such as rheumatoid arthritis, psoriasis or inflammatory bowel diseases or other autoimmune and inflammatory disorders.

IL12 receptor beta 1 (IL12Rβ1) chain is known as a potential therapeutic target for the treatment of Th1/Th17 mediated disorders, such as psoriasis and other autoimmune and inflammatory disorders. Psoriasis is a common chronic inflammatory skin disease characterized by hyper-proliferation of the epidermal layer and a prominent infiltrate of dendritic cells and T cells. T cells play a key role in the pathological reactions occurring in the skin by secreting type 1 cytokines (including IFN-γ and TNF-α) and that induce keratinocyte hyperproliferation, angiogenesis and neutrophil infiltration.

Two cytokines that are thought to be important in the development of Th1 immune responses in psoriasis are interleukin-12 (IL12) and interleukin-23 (IL23). Both cytokines are produced by antigen-presenting cells, such as macrophages and dendritic cells, and function by activating T cells and natural killer cells. IL12 and IL23 are members of a heterodimeric family of soluble cytokines that are comprised of p35/p40 protein subunits in IL12 and p19/p40 protein subunits in IL23. The IL12 p40 subunit of either cytokine binds to the transmembrane IL12 receptor β1 (IL12Rβ1) that is found on the surface of immune cells. Interruption of the IL12 p40/IL12Rβ1 interaction may prevent the biological activity of both IL12 and IL23.

Several inflammatory and autoimmune diseases including psoriasis are linked to exacerbated Th1 and/or Th17 responses. Many of them are currently treated either with general immuno-suppressants or very selectively acting biologicals such as anti-TNF-α antibodies that are not effective in all patients. These were found to increase the risk for infections and to become ineffective after repeated treatment. Therefore, there is an unmet medical need for treatments with increased safety profiles and simultaneous capacity to induce long-term remission or cure of the disease.

A neutralizing antibody to IL12p40 successfully abolished psoriatic lesions in mice, even when administered after transfer of the T cell subset that induced the psoriasis-like condition (Hong et al., J. Immunol. 162.12 (1999): 7480-91.). An anti-IL12p40 antibody targeting both IL12 and IL23 is currently in clinical trials for Psoriasis (Kauffman et al. J. Invest Dermatol. 123.6 (2004): 1037-44, Papp et al. Lancet. 371.9625 (2008): 1675-84, Kimball et al. Arch. Dermatol. 144.2 (2008): 200-07), Crohns Disease (Sandborn et al., Gastroenterology. 135.4 (2008): 1130-41) and Multiple Sclerosis (Segal et al., Lancet Neurol. 7.9 (2008): 796-804). Targeting IL12Rβ1 and hence, differentiation and maintenance of Th1 and Th17 cell populations as well as the IL12 and IL23 mediated inflammatory cytokine production by these cells, offers an opportunity for an improved therapeutic agent.

U.S. Pat. No. 6,046,012 refers to IL12Rβ1 and antibodies binding to anti-IL12Rβ1 in general. Anti-mouse IL12Rβ1 monoclonal antibodies are also commercialized by Becton Dickinson (Cat#551455).

However, to date, there is no description in the art of binding molecules to human IL12Rβ1 showing IL12Rβ1 antagonistic activity, for use in the treatment of autoimmune and inflammatory disorders, such as psoriasis or Crohn's disease. Only indirect evidence by targeting the respective interaction partner (IL12p40) validates the pathway.

Therefore, in one aspect, the invention provides an antibody or binding protein comprising an antigen-binding portion of said antibody for a target in IL12Rβ1 polypeptide (SEQ ID NO:41), characterized in that the antibody or binding protein specifically binds to IL12Rβ1 polypeptide. In one embodiment, the antibody of the invention is from a mammal, having an origin such as human or camelid, or is a humanized antibody. In a particular embodiment, the anti-IL12Rβ1 antibody is characterized as having antigen-binding region that is specific for the target protein IL12Rβ1 and binds to IL12Rβ1 or a fragment of IL12Rβ1.

In one embodiment, the antibodies according to the invention are IL12Rβ1 antagonists with no or low agonistic activity. In certain embodiments, the antibodies bind the target protein IL12Rβ1 and inhibit IL12 dependent IFN-γ production in human blood cells.

In another embodiment, the antibodies according to the invention competitively inhibit IL12 and IL23 binding to IL12Rβ1. More preferably, the antibodies are IL12Rβ1 antagonist with no agonistic activity.

The binding may be determined by one or more assays that can be used to measure an activity which is either antagonism or agonism by the antibody. Preferably, the assays measure at least one of the effects of the antibody on IL12Rβ1 that include: IL12 dependent IFN-γ production in human blood cells, IL23/IL17 dependent IFN-γ production in human blood cells, IL12 ex vivo IFN-γ production in primate blood cells.

In another embodiment, the invention provides antibodies that specifically bind to common IL12/IL23 p40 ligand binding region of IL12Rβ1.

According to another particular embodiment, the antibodies bind to IL12Rβ1 with a $K_D$ of 100 nM or less, 10 nM or less, 1 nM or less, and inhibit IL12 and IL23 binding to IL12Rβ1 polypeptide with an $IC_{50}$ around 10 nM or less, 1 nM or less, 100 µM or less as measured in an in vitro competitive binding assay.

In another alternative embodiment, the antibodies bind specifically to IL12Rβ1 and inhibit selectively IL12 binding to IL12Rβ1 polypeptide, but not IL23 binding, with an $IC_{50}$ around 10 nM or less, 1 nM or less, 100 µM or less as measured in an in vitro competitive binding assay.

In another embodiment, the antibodies inhibit IL12 dependent IFNγ production in human blood cells with an $IC_{50}$ around 10 nM or less, 1 nM or less or 100 µM or less.

In another related embodiment, the antibodies are capable of ameliorating the disease in an IBD mouse model as compared to untreated control animals. In another related embodiment, the antibodies are capable of completely blocking the IFNγ response for extended times in peripheral blood mononuclear cells of cynomolgous monkeys treated with a single dose. In a PK/PD study, anti-IL12Rβ1 mAb plasma levels above 10 µg/ml resulted in complete suppression of ex-vivo IL12 induced IFNγ production.

In another embodiment, the antibodies block the heterodimerization of IL12Rβ1 with its subunit IL12Rβ2 and/or IL23R.

In some particular embodiments, the antibodies of the invention do not cross-react with at least one other cytokine receptor. In a specific embodiment, the antibodies of invention do not cross-react with human IL4Rα receptor.

In a preferred embodiment, the antibodies of the invention cross-react at least with rodent or primate IL12Rβ1 receptor.

In another related embodiment, the antibodies according to the invention are fully human or humanized IgG4 antibodies or silent mutant IgG1 antibodies with no antibody dependent cellular cytotoxicity (ADCC) activity and inhibit IL12 dependent IFNγ production in human blood cells with an $IC_{50}$ around 10 nM or less, 1 nM or less or 100 μM or less.

The invention also relates to binding protein comprising an antigen-binding portion of said antibody for a target in IL12Rβ1 polypeptide (SEQ ID NO: 41), wherein said antigen-binding portion is pegylated. In a related embodiment, the pegylated antigen-binding portion is a pegylated Fab.

The present invention relates to isolated antibodies, particularly human or humanized antibodies, that inhibit IL12 and IL23 binding to IL12Rβ1 and that inhibit IL12 dependent IFNγ production in human blood cells. In certain embodiments, the antibodies of the invention are derived from particular heavy and light chain sequences and/or comprise particular structural features such as CDR regions comprising particular amino acid sequences. The invention provides isolated antibodies, methods of making such antibodies, immunoconjugates and multivalent or multispecific molecules comprising such antibodies and pharmaceutical compositions containing the antibodies, immunoconjugates or bispecific molecules of the invention. The invention also relates to methods of using the antibodies to inhibit, i.e., antagonize, function of IL12Rβ1 in order to inhibit development of a disorder or condition mediated by IL12, IL23 and/or IL12Rβ1, for example, resulting in the treatment of a pathological disorder that is mediated by IL12Rβ1 or that can be treated by inhibiting IFNγ production in blood cells; for example, Th1/Th17 mediated disorders such as rheumatoid arthritis, psoriasis and inflammatory bowel diseases.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" or "signaling activity" refers to a biochemical causal relationship generally initiated by a protein-protein interaction such as binding of a growth factor to a receptor, resulting in transmission of a signal from one portion of a cell to another portion of a cell. In general, the transmission involves specific phosphorylation of one or more tyrosine, serine, or threonine residues on one or more proteins in the series of reactions causing signal transduction. Penultimate processes typically include nuclear events, resulting in a change in gene expression.

The term IL12Rβ1 or IL12 receptor beta 1 refers to human IL12Rβ1 as defined in SEQ ID NO: 41.

The term "antibody" as referred to herein includes whole antibodies and any antigen binding fragment (i.e., "antigen-binding portion") or single chains thereof. A binding protein comprising the antigen-binding portion of an antibody is also intended to be encompassed within the term "antibody". In particular, the term "antibody that binds to IL12Rβ1" is intended to encompass IL12Rβ1 binding proteins comprising the IL12Rβ1-binding portion of an antibody.

A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen (e.g., a portion of IL12Rβ1). It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds IL12Rβ1 is substantially free of antibodies that specifically bind other antigens than IL12Rβ1). An isolated antibody that specifically binds IL12Rβ1 may, however, have cross-reactivity to other antigens, such as IL12Rβ1 molecules from other species. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences or antibody containing consensus framework sequences derived from human framework sequences analysis, for example, as described in Knappik, et al. (2000. J Mol Biol 296, 57-86).

The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG4) that is provided by the heavy chain constant region genes.

The phrases "an antibody recognizing an antigen" and "an antibody specific for an antigen" are used interchangeably herein with the term "an antibody which binds specifically to an antigen".

As used herein, an antibody that "specifically binds to IL12Rβ1 polypeptide" is intended to refer to an antibody that binds to human IL12Rβ1 polypeptide with a $K_D$ of a 100 nM or less, 10 nM or less, 1 nM or less. An antibody that "cross-reacts with an antigen other than IL12Rβ1" is intended to refer to an antibody that binds that antigen with a $K_D$ of $0.5 \times 10^{-8}$ M or less, $5 \times 10^{-9}$ M or less, or $2 \times 10^{-9}$ M or less. An antibody that "does not cross-react with a particular antigen" is intended to refer to an antibody that binds to that antigen, with a $K_D$ of $1.5 \times 10^{-8}$ M or greater, or a $K_D$ of $5-10 \times 10^{-8}$ M or $1 \times 10^{-7}$ M or greater. In certain embodiments, such antibodies that do not cross-react with the antigen exhibit essentially undetectable binding against these proteins in standard binding assays.

As used herein, the term "antagonist" is intended to refer to an antibody that inhibits IL12Rβ1 induced signaling activity in the presence of IL12 in a human cell assay such as IL12 dependent IFNγ production assay in human blood cell. Examples of IL12 dependent IFNγ production assay in human blood cell and IL23 dependent IFNγ production assay in human blood cell are described in more details in the examples below. In some embodiments, the antibodies inhibit IFNγ production as measured in a human blood cell assay at an $IC_{50}$ of 10 nM or less, 1 nM or less, or 100 μM or less.

As used herein, an antibody with "no agonistic activity" is intended to refer to an antibody that does not significantly increase IL12Rβ1 mediated signaling activity in the absence of IL12 in a cell-based assay, such as human blood cells IFNγ production assay. Such assays are described in more details in the examples below.

As used herein, an antibody or binding protein that inhibits IL12 and IL23 binding to IL12Rβ1 polypeptide is intended to refer to an antibody that inhibits IL12 and IL23 binding to IL12Rβ1 polypeptide with an $EC_{50}$ of 10 nM or less, preferably with an $EC_{50}$ of 1 nM or less, more preferably with an $EC_{50}$ of 100 μM, or less, as measured in an in vitro competitive binding assay such as Bioveris™ assay. Such assays are described in more details in the examples below.

As used herein, an antibody or binding protein that inhibits IL12 ex vivo IFNγ production in primate blood cell is intended to refer to an antibody that decreases IL12 ex vivo IFNγ production to a level below 10% of the control level with an anti-IL12Rβ1 mAb plasma level above 10 μg/ml. In some embodiments, it refers to antibodies that completely abolish IL12 ex vivo IFNγ production in primate blood cell with anti-IL12Rβ1 mAb plasma levels above 10 μg/ml. Such assays are described in more details in the examples below.

The term "$K_{assoc}$" or "$K_a$", as used herein, is intended to refer to the association rate of a particular antibody-antigen interaction, whereas the term "$K_{dis}$" or "$K_d$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

In order to get a higher avidity probe, a dimeric conjugate (two molecules of an antibody protein coupled to a FACS marker) can be constructed, thus making low affinity interactions (such as with the germline antibody) more readily detected by FACS. In addition, another means to increase the avidity of antigen binding involves generating dimers, trimers or multimers of any of the constructs described herein of the anti-IL12Rβ1 antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in IL12Rβ1 hybrids to create such higher order structures. For example, it is possible to use multimerizing domains such as trimerizing domain described in Borean (WO2004039841).

As used herein, the term "selectivity" for an antibody refers to an antibody that binds to a certain target polypeptide but not to closely related polypeptides.

As used herein, the term "high affinity" for an antibody refers to an antibody having a $K_D$ of 1 nM or less for a target antigen. As used herein, the term "subject" includes any human or nonhuman animal.

The term "nonhuman animal" includes all vertebrates, e.g., mammals and non-mammals, such as nonhuman primates, sheep, dogs, cats, horses, cows, chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia*, a cell of *Trichoderma*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in CHO mammalian cells; however optimized expression of these sequences in other eukaryotic cells is also envisioned herein. The amino acid sequences encoded by optimized nucleotide sequences are also referred to as optimized.

Standard assays to evaluate the binding ability of the antibodies toward IL12Rβ1 of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of IL12Rβ1 (e.g., receptor binding, IL12 or IL23 ligand binding inhibition, inhibiting IL12 induced IFNγ production) are described in further detail in the Examples.

Accordingly, an antibody that "inhibits" one or more of these IL12Rβ1 functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits IL12Rβ1 activity effects such a statistically significant decrease by at least 10% of the measured parameter, by at least 50%, 80% or 90%, and in certain embodiments an antibody of the invention may inhibit greater than 95%, 98% or 99% of IL12Rβ1 functional activity.

The terms "cross-block", "cross-blocked" and "cross-blocking" are used interchangeably herein to mean the ability of an antibody or other binding agent to interfere with the binding of other antibodies or binding agents to IL12Rβ1 in a standard competitive binding assay.

The ability or extent to which an antibody or other binding agent is able to interfere with the binding of another antibody or binding molecule to IL12Rβ1, and therefore whether it can be said to cross-block according to the invention, can be determined using standard competition binding assays. One suitable assay involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

Further details on these methods are given in the Examples.

According to the invention, a cross-blocking antibody or other binding agent according to the invention binds to IL12Rβ1 in the described BIAcore cross-blocking assay such that the recorded binding of the combination (mixture) of the antibodies or binding agents is between 80% and 0.1% (e.g. 80% to 4%) of the maximum theoretical binding, specifically between 75% and 0.1% (e.g. 75% to 4%) of the maximum theoretical binding, and more specifically between 70% and 0.1% (e.g. 70% to 4%), and more specifically between 65% and 0.1% (e.g. 65% to 4%) of maximum theoretical binding (as defined above) of the two antibodies or binding agents in combination An antibody is defined as cross-blocking in the ELISA assay as described in the Examples, if the solution phase anti-IL12Rβ1 antibody is able to cause a reduction of between 60% and 100%, specifically between 70% and 100%, and more specifically between 80% and 100%, of the IL12Rβ1 detection signal (i.e. the amount of IL12Rβ1 bound by the coated antibody) as compared to the IL12Rβ1 detection signal obtained in the absence of the solution phase anti-IL12Rβ1 antibody (i.e. the positive control wells).

Recombinant Antibodies

Antibodies of the invention include the human recombinant antibodies, isolated and structurally characterized as described, in the Examples. The $V_H$ amino acid sequences of isolated antibodies according to the invention are shown in SEQ ID NOs: 29-32. The $V_L$ amino acid sequences of isolated antibodies of the invention are shown in SEQ ID NOs: 25-28 respectively. Other antibodies of the invention include amino acids that have been mutated by amino acid deletion, insertion or substitution, yet have at least 60, 70, 80, 90 or 95 percent identity in the CDR regions with the CDR regions depicted in the sequences described above. In some embodiments, it include mutant amino acid sequences wherein no more than 1, 2, 3, 4 or 5 amino acids have been mutated by amino acid deletion, insertion or substitution in the CDR regions when compared with the CDR regions depicted in the sequence described above.

Variable light chain nucleotide sequences are shown in SEQ ID NOs 33-36. Variable heavy chain nucleotide sequences are shown in SEQ ID NOs 37-40. Other nucleic acids encoding antibodies of the invention include nucleic acids that have been mutated, yet have at least 60, 70, 80, 90 or 95 percent identity to the sequences described above. In some embodiments, it include variant nucleic acids wherein no more than 1, 2, 3, 4 or 5 nucleotide have been changed by nucleotide deletion, insertion or substitution in the variable regions when compared with the variable regions depicted in the sequence described above.

For antibodies that bind to the same epitope, the $V_H$, $V_L$, full length light chain, and full length heavy chain sequences (nucleotide sequences and amino acid sequences) can be "mixed and matched" to create other anti-IL12Rβ1 binding molecules of the invention. IL12Rβ1 binding of such "mixed and matched" antibodies can be tested using the binding assays described above and in the Examples (e.g., ELISAs). When these chains are mixed and matched, a $V_H$ sequence from a particular $V_H/V_L$ pairing should be replaced with a structurally similar $V_H$ sequence. Likewise a full length heavy chain sequence from a particular full length heavy chain/full length light chain pairing should be replaced with a structurally similar full length heavy chain sequence. Likewise, a $V_L$ sequence from a particular $V_H/V_L$ pairing should be replaced with a structurally similar $V_L$ sequence. Likewise a full length light chain sequence from a particular full length heavy chain/full length light chain pairing should be replaced with a structurally similar full length light chain sequence. Accordingly, in one aspect, the invention provides an isolated recombinant antibody having: a heavy chain variable region comprising an amino acid sequence selected from the group consisting of SEQ ID NOs: 29-32; and a light chain variable region comprising an amino acid sequence selected from the group consisting of SEQ ID NOs: 25-28; wherein the antibody specifically binds to IL12Rβ1.

In another aspect, the invention provides an isolated recombinant antibody having: a full length heavy chain comprising a $V_H$ amino acid sequence selected from the group consisting of SEQ ID NOs: 29-32; and a full length light chain comprising a $V_L$ amino acid sequence selected from the group consisting of SEQ ID NOs:25-28; wherein the antibody specifically binds to IL12Rβ1.

In another aspect, the invention provides an isolated recombinant antibody having: a full length heavy chain encoded by a nucleotide sequence comprising a sequence selected from the group consisting of SEQ ID NOs: 37-40; and a full length light chain encoded by a nucleotide sequence comprising a sequence selected from the group consisting of SEQ ID NOs: 33-36; wherein the antibody specifically binds to IL12Rβ1.

Examples of amino acid sequences of the $V_H$ CDR1s of antibodies according to the invention are shown in SEQ ID NOs: 1-4. Examples of amino acid sequences of the $V_H$ CDR2s of antibodies according to the invention are shown in SEQ ID NOs: 5-8. Examples of amino acid sequences of the $V_H$ CDR3s of antibodies according to the invention are shown in SEQ ID NOs: 8-12. Examples of amino acid sequences of the $V_L$ CDR1s of antibodies according to the invention are shown in SEQ ID NOs: 13-16. Examples of amino acid sequences of the $V_L$ CDR2s of antibodies according to the invention are shown in SEQ ID NOs: 17-20. The amino acid sequences of the $V_L$ CDR3s of antibodies according to the invention are shown in SEQ ID NOs: 21-24. The CDR regions are delineated using the Kabat system (Kabat, E. A., et al., 1991 Sequences of Proteins of Immunological Interest, Fifth Edition, U.S. Department of Health and Human Services, NIH Publication No. 91-3242).

Given that each of these antibodies can bind to IL12Rβ1 and that antigen-binding specificity is provided primarily by the CDR1, 2 and 3 regions, the $V_H$ CDR1, 2 and 3 sequences and $V_L$ CDR1, 2 and 3 sequences can be "mixed and matched" (i.e., CDRs from different antibodies can be mixed and match, each antibody containing a $V_H$ CDR1, 2 and 3 and a $V_L$ CDR1, 2 and 3 create other anti-IL12Rβ1 binding molecules of the invention. IL12Rβ1 binding of such "mixed and matched" antibodies can be tested using the binding assays described above and in the Examples (e.g., ELISAs). When $V_H$ CDR sequences are mixed and matched, the CDR1, CDR2 and/or CDR3 sequence from a particular $V_H$ sequence should be replaced with a structurally similar CDR sequence(s). Likewise, when $V_L$ CDR sequences are mixed and matched, the CDR1, CDR2 and/or CDR3 sequence from a particular $V_L$ sequence should be replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences shown herein for monoclonal antibodies of the present invention.

An isolated recombinant antibody, or antigen binding region thereof has: a heavy chain variable region CDR1 comprising an amino acid sequence selected from the group consisting of SEQ ID NOs: 1-4; a heavy chain variable region CDR2 comprising an amino acid sequence selected from the group consisting of SEQ ID NOs: 5-8; a heavy chain variable region CDR3 comprising an amino acid sequence selected from the group consisting of SEQ ID NOs: 9-12; a light chain variable region CDR1 comprising an amino acid sequence selected from the group consisting of SEQ ID NOs: 13-16; a light chain variable region CDR2 comprising an amino acid sequence selected from the group consisting of SEQ ID NOs: 17-20; and a light chain variable region CDR3 comprising an amino acid sequence selected from the group consisting of SEQ ID NOs: 21-24; wherein the antibody specifically binds to IL12Rβ1.

In a certain embodiment, the antibody comprises: a heavy chain variable region CDR1 of SEQ ID NO: 1; a heavy chain variable region CDR2 of SEQ ID NO: 5; a heavy chain variable region CDR3 of SEQ ID NO: 9; a light chain variable region CDR1 of SEQ ID NO: 13; a light chain variable region CDR2 of SEQ ID NO: 17; and a light chain variable region CDR3 of SEQ ID NO: 21.

In a certain embodiment, the antibody comprises: a heavy chain variable region CDR1 of SEQ ID NO: 2; a heavy chain variable region CDR2 of SEQ ID NO: 6; a heavy chain variable region CDR3 of SEQ ID NO: 10; a light chain variable region CDR1 of SEQ ID NO: 14; a light chain variable region CDR2 of SEQ ID NO: 18; and a light chain variable region CDR3 of SEQ ID NO: 22.

In a certain embodiment, the antibody comprises: a heavy chain variable region CDR1 of SEQ ID NO: 3; a heavy chain variable region CDR2 of SEQ ID NO: 7; a heavy chain variable region CDR3 of SEQ ID NO: 11; a light chain variable region CDR1 of SEQ ID NO: 15; a light chain variable region CDR2 of SEQ ID NO: 19; and a light chain variable region CDR3 of SEQ ID NO: 23.

In a certain embodiment, the antibody comprises: a heavy chain variable region CDR1 of SEQ ID NO: 4; a heavy chain variable region CDR2 of SEQ ID NO: 8; a heavy chain variable region CDR3 of SEQ ID NO: 12; a light chain variable region CDR1 of SEQ ID NO: 16; a light chain variable region CDR2 of SEQ ID NO: 20; and a light chain variable region CDR3 of SEQ ID NO: 24.

As used herein, a human antibody comprises heavy or light chain variable regions or full length heavy or light chains that are "the product of" or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutation. However, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody may display no more than 5, or even no more than 4, 3, 2, or 1 amino acid difference from the amino acid sequence encoded by the germline immunoglobulin gene.

Homologous Antibodies

In yet another embodiment, an antibody of the invention has full length heavy and light chain amino acid sequences; full length heavy and light chain nucleotide sequences, variable region heavy and light chain nucleotide sequences, or variable region heavy and light chain amino acid sequences that are homologous to the amino acid and nucleotide sequences of the antibodies described herein, and wherein the antibodies retain the desired functional properties of the anti-IL12Rβ1 antibodies of the invention.

For example, the invention provides an isolated recombinant antibody (or a binding protein comprising an antigen binding portion thereof) comprising a heavy chain variable region and a light chain variable region, wherein: the heavy chain variable region is at least 80%, or at least 90% identical to an amino acid sequence selected from the group consisting of SEQ ID NOs:29-32; the light chain variable region is at least 80%, or at least 90% identical to an amino acid sequence selected from the group consisting of SEQ ID NOs:25-28; the antibody specifically binds to IL12Rβ1, and the antibody exhibits at least one of the following functional properties: it inhibits IL12 and IL23 binding to IL12Rβ1, it inhibits IL12 dependent IFNγ production in human blood cell, it inhibits IL23 dependent IFNγ production in human blood cell, or it inhibits IL12 ex vivo IFN-γ production in primate blood cells.

In another example, the invention provides an isolated recombinant antibody comprising a full length heavy chain and a full length light chain, wherein: the variable heavy chain is encoded by a nucleotide sequence that is at least 80%, or at least 90% identical to a nucleotide sequence selected from the group consisting of SEQ ID NOs 37-40; the variable light chain is encoded by a nucleotide sequence that is at least 80%, or at least 90% identical to a nucleotide sequence selected from the group consisting of SEQ ID NOs 33-36; the antibody specifically binds to IL12Rβ1, and the antibody exhibits at least one of the following functional properties: it inhibits IL12 and IL23 binding to IL12Rβ1, it inhibits IL12 dependent IFNγ production in human blood cells, it inhibits IL23 dependent IFNγ production in human blood cells, or it inhibits IL12 ex vivo IFN-γ production in primate blood cells.

In various embodiments, the antibody may exhibit one or more, two or more, three or more, or four of the functional properties discussed above. The antibody can be, for example, a human antibody, a humanized antibody or a chimeric antibody. Preferably the antibody is a fully human silent IgG1 antibody.

In other embodiments, the $V_H$ and/or $V_L$ amino acid sequences may be 50%, 60%, 70%, 80%, 90%, 95%, 96%, 97%, 98% or 99% identical to the sequences set forth above. In other embodiments, the $V_H$ and/or $V_L$ amino acid sequences may be identical except an amino acid substitution in no more than 1, 2, 3, 4 or 5 amino acid position. An antibody having $V_H$ and $V_L$ regions having high (i.e., 80% or greater) identity to the $V_H$ and $V_L$ regions of SEQ ID NOs 29-32 and SEQ ID NOs 25-28 respectively, can be obtained by mutagenesis (e.g., site-directed or PCR-mediated mutagenesis) of nucleic acid molecules encoding SEQ ID NOs: 37-40 and 33-36 respectively, followed by testing of the encoded altered antibody for retained function (i.e., the functions set forth above) using the functional assays described herein.

As used herein, the percent identity between the two sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. Alternatively, the percent identity between two amino acid sequences can be determined using the Needleman and Wunsch (J. Mol, Biol. 48:444-453, 1970) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6.

Antibodies with Conservative Modifications

In certain embodiments, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the anti-IL12Rβ1 antibodies of the invention. Accordingly, the invention provides an isolated recombinant antibody, comprising an antigen-binding portion consisting of a heavy chain variable region comprising CDR1, CDR2, and CDR3 sequences and a light chain variable region comprising CDR1, CDR2, and CDR3 sequences, wherein: the heavy chain variable region CDR1 amino acid sequences are selected from the group consisting of SEQ ID NOs:1-4, and conservative modifications thereof; the heavy chain variable region CDR2 amino acid sequences are selected from the group consisting of SEQ ID NOs: 5-8, and conservative modifications thereof; the heavy chain variable region CDR3 amino acid sequences are selected from the group consisting of SEQ ID NOs: 9-12, and conservative modifications thereof; the light chain variable regions CDR1 amino acid sequences are selected from the group consisting of SEQ ID NOs: 13-16, and conservative modifications thereof; the light chain variable regions CDR2 amino acid sequences are selected from the group consisting of SEQ ID NOs: 17-20, and conservative modifications thereof; the light chain variable regions of CDR3 amino acid sequences are selected from the group consisting of SEQ ID NOs: 21-24, and conservative modifications thereof; the antibody specifically binds to IL12Rβ1, and the antibody exhibits at least one of the following functional properties: it inhibits IL12 and IL23 binding to IL12Rβ1, it inhibits IL12 dependent IFNγ production in human blood cells, it inhibits IL23 dependent IFNγ production in human blood cells, or it inhibits IL12 ex vivo IFN-γ production in primate blood cells.

In various embodiments, the antibody may exhibit one or more, two or more, three or more, or four of the functional properties listed discussed above. Such antibodies can be, for example, human antibodies, humanized antibodies or chimeric antibodies.

In other embodiments, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the anti-IL12Rβ1 antibodies of the invention. Accordingly, the invention provides an isolated monoclonal antibody optimized for expression in a mammalian cell consisting of a full length heavy chain and a full length light chain wherein: the full length heavy chain comprises variable amino acid sequences selected from the group of SEQ ID NOs: 29-32, and conservative modifications thereof; and the full length light chain comprises variable amino acid sequences selected from the group of SEQ ID NOs: 25-28, and conservative modifications thereof; the antibody specifically binds to IL12Rβ1; and the antibody exhibits at least one of the following functional properties: it inhibits IL12 and IL23 binding to IL12Rβ1, it inhibits IL12 dependent IFNγ production in human blood cells, it inhibits IL23 dependent IFNγ production in human blood cells, or it inhibits IL12 ex vivo IFN-γ production in primate blood cells.

In various embodiments, the antibody may exhibit one or more, two or more, or three or more, or four of the functional properties listed discussed above. Such antibodies can be, for example, human antibodies, humanized antibodies or chimeric antibodies.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Modifications can be introduced into an antibody of the invention by standard techniques known in the art, such as site-directed mutagenesis and PCR-mediated mutagenesis.

Antibodies that Bind to the Same Epitope as Anti-IL12Rβ1 Antibodies of the Invention In another embodiment, the invention provides antibodies that bind to the same epitope as do the various specific anti-IL12Rβ1 antibodies of the invention described herein.

Additional antibodies can therefore be identified based on their ability to cross-compete (e.g., to competitively inhibit the binding of), in a statistically significant manner with other antibodies of the invention in standard IL12Rβ1 binding assays. The ability of a test antibody to inhibit the binding of antibodies of the present invention to human IL12Rβ1 demonstrates that the test antibody can compete with that antibody for binding to human IL12Rβ1; such an antibody may, according to non-limiting theory, bind to the same or a related (e.g., a structurally similar or spatially proximal) epitope on human IL12Rβ1 as the antibody with which it competes. In a certain embodiment, the antibody that binds to the same epitope on human IL12Rβ1 as the antibodies of the present invention is a human recombinant antibody. Such human recombinant antibodies can be prepared and isolated as described in the Examples.

Engineered and Modified Antibodies

An antibody of the invention further can be prepared using an antibody having one or more of the $V_H$ and/or $V_L$ sequences shown herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to Winter, and U.S. Pat. Nos. 5,530,101; 5,585,089; 5,693,762 and 6,180,370 to Queen et al.)

Accordingly, another embodiment of the invention pertains to an isolated monoclonal anti-IL12Rβ1 antibody, comprising a heavy chain variable region comprising CDR1 sequences having an amino acid sequence selected from the group consisting of SEQ ID NOs:1-4; CDR2 sequences having an amino acid sequence selected from the group consisting of SEQ ID NOs:5-8; CDR3 sequences having an amino acid sequence selected from the group consisting of SEQ ID NOs:9-12, respectively; and a light chain variable region having CDR1 sequences having an amino acid sequence selected from the group consisting of SEQ ID NOs: 13-16; CDR2 sequences having an amino acid sequence selected from the group consisting of SEQ ID NOs: 17-20; and CDR3 sequences having an amino acid sequence selected from the group consisting of SEQ ID NOs: 21-24, respectively. Thus, such antibodies contain the $V_H$ and $V_L$ CDR sequences of monoclonal antibodies, yet may contain different framework sequences from these antibodies.

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam. ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. Mol. Biol. 227:776-798; and Cox, J. P. L. et al., 1994 Eur. J. Immunol. 24:827-836.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Accordingly, in another embodiment, the invention provides isolated anti-IL12Rβ1 monoclonal antibodies comprising a heavy chain variable region having: a $V_H$ CDR1 region consisting of an amino acid sequence selected from the group having SEQ ID NOs: 1-4 or an amino acid sequence having one, two, three, four or five amino acid substitutions, deletions or additions as compared to SEQ ID NOs: 1-4; a $V_H$ CDR2 region having an amino acid sequence selected from the group consisting of SEQ ID NOs: 5-8, or an amino acid sequence having one, two, three, four or five amino acid substitutions, deletions or additions as compared to SEQ ID NOs: 5-8; a $V_H$ CDR3 region having an amino acid sequence selected from the group consisting of SEQ ID NOs: 9-12, or an amino acid sequence having one, two, three, four or five amino acid substitutions, deletions or additions as compared to SEQ ID NOs: 9-12; a $V_L$ CDR1 region having an amino acid sequence selected from the group consisting of SEQ ID NOs: 13-16, or an amino acid sequence having one, two, three, four or five amino acid substitutions, deletions or additions as compared to SEQ ID NOs: 13-16; a $V_L$ CDR2 region having an amino acid sequence selected from the group consisting of SEQ ID NOs: 17-20, or an amino acid sequence having one, two, three, four or five amino acid substitutions, deletions or additions as compared to SEQ ID NOs: 17-20; and a $V_L$ CDR3 region having an amino acid sequence selected from the group consisting of SEQ ID NOs: 21-24, or an amino acid sequence having one, two, three, four or five amino acid substitutions, deletions or additions as compared to SEQ ID NOs: 21-24.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to IL12Rβ1. Such frameworks or scaffolds include the 5 main idiotypes of human immunoglobulins, or fragments thereof (such as those disclosed elsewhere herein), and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target protein of SEQ ID NO: 41. Such compounds are referred herein as "polypeptides comprising a target-specific binding region". Examples of non-immunoglobulin framework are further described in the sections below (camelid antibodies and non-antibody scaffold).

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as $V_{HH}$ can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschberger, M. et al. 2003 Bioconjugate Chem 14: 440-448; Cortez-Retamozo, V. et al. 2002 Int J Cancer 89: 456-62; and Lauwereys, M. et al. 1998 EMBO J. 17: 3512-3520. Engineered libraries of camelid antibodies and antibody fragments are commercially available, for example, from Ablynx, Ghent, Belgium. As with other antibodies of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for IL12Rβ1. In certain embodiments herein, the camelid antibody or nanobody is naturally produced in the camelid animal, i.e., is produced by the camelid following immunization with IL12Rβ1 or a peptide fragment thereof, using techniques described herein for other antibodies. Alternatively, the anti-IL12Rβ1 camelid nanobody is engineered, i.e., produced by selection for example from a library of phage displaying appropriately mutagenized camelid nanobody proteins using panning procedures with IL12Rβ1 as a target as described in the examples herein. For example, the anti-IL12Rβ1 camelid nanobody is selected among those that inhibit IL12 and IL23 binding to IL12Rβ1 and/or inhibit IL12 induced IFNγ production in human blood cells, and/or inhibit IL23 induced IFNγ production in human blood cells, the corresponding assays being described in the Examples.

Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Non-Antibody Scaffold

Known non-immunoglobulin frameworks or scaffolds include, but are not limited to, Adnectins (fibronectin) (Compound Therapeutics, Inc., Waltham, Mass.), ankyrin (Molecular Partners AG, Zurich, Switzerland), domain antibodies (Domantis, Ltd (Cambridge, Mass.) and Ablynx nv (Zwijnaarde, Belgium)), lipocalin (Anticalin) (Pieris Proteolab AG, Freising, Germany), small modular immunopharmaceuticals (Trubion Pharmaceuticals Inc., Seattle, Wash.), maxybodies (Avidia, Inc. (Mountain View, Calif.)), Protein A (Affibody AG, Sweden) and affilin (gamma-crystallin or ubiquitin) (Scil Proteins GmbH, Halle, Germany), protein epitope mimetics (Polyphor Ltd, Allschwil, Switzerland).

(i) Fibronectin Scaffold

The fibronectin scaffolds are based preferably on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (U.S. Pat. No. 6,818,418).

These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity to those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

(ii) Ankyrin—Molecular Partners

The technology is based on using proteins with ankyrin derived repeat modules as scaffolds for bearing variable regions which can be used for binding to different targets. The ankyrin repeat module is a 33 amino acid polypeptide consisting of two anti-parallel α-helices and a β-turn. Binding of the variable regions is mostly optimized by using ribosome display.

(iii) Maxybodies/Avimers—Avidia

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, 20040175756; 20050053973; 20050048512; and 20060008844.

(vi) Protein A—Affibody

Affibody® affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate Affibody® libraries with a large number of ligand variants (See e.g., U.S. Pat. No. 5,831,012). Affibody® molecules mimic antibodies; they have a molecular weight of 6 kDa, compared to the molecular weight of antibodies, which is 150 kDa. In spite of its small size, the binding site of Affibody® molecules is similar to that of an antibody.

(v) Anticalins—Pieris

Anticalins® are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids.

The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain.

The set of four loops, which makes up the binding pocket, shows pronounced structural plasticity and tolerates a variety of side chains. The binding site can thus be reshaped in a proprietary process in order to recognize prescribed target molecules of different shape with high affinity and specificity.

One protein of lipocalin family, the bilin-binding protein (BBP) of Pieris Brassicae has been used to develop anticalins by mutagenizing the set of four loops. One example of a patent application describing "anticalins" is PCT WO 199916873.

(vi) Affilin—Scil Proteins

Affilin™ molecules are small non-immunoglobulin proteins which are designed for specific affinities towards proteins and small molecules. New Affilin™ molecules can be very quickly selected from two libraries, each of which is based on a different human derived scaffold protein.

Affilin™ molecules do not show any structural homology to immunoglobulin proteins. Scil Proteins employs two Affilin™ scaffolds, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368

(vii) Protein Epitope Mimetics (PEM)

PEM are medium-sized, cyclic, peptide-like molecules (MW 1-2 kDa) mimicking beta-hairpin secondary structures of proteins, the major secondary structure involved in protein-protein interactions.

Framework or Fc Engineering

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et at.

In another embodiment, one or more amino acid residues are altered to thereby alter the ability of the antibody to fix complement. This approach is described further in PCT Publication WO 94/29351 by Bodmer et at.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγRI, FcγRII, FcγRIII and FcRn have been mapped and variants with improved binding have been described (see Shields, R. L. et al., 2001 J. Biol. Chen. 276:6591-6604).

In certain embodiments, the Fc domain of IgG1 isotype is used. In some specific embodiments, a mutant variant of IgG1 Fc fragment is used, e.g. a silent IgG1 Fc which reduces or eliminates the ability of the fusion polypeptide to mediate antibody dependent cellular cytotoxicity (ADCC) and/or to bind to an Fcγ receptor. An example of an IgG1 isotype silent mutant wherein Leucine residue is replaced by Alanine residue at amino acid positions 234 and 235 as described in J. Virol 2001 December; 75(24):12161-8 by Hezareh et al.

In certain embodiments, the Fc domain is a mutant preventing glycosylation at residue at position 297 of Fc domain. For example, the Fc domain contains an amino acid substitution of asparagine residue at position 297. Example of such amino acid substitution is the replacement of N297 by a glycine or an alanine.

In still another embodiment, the glycosylation of an antibody is modified. For example, an aglycoslated antibody can be made (i.e., the antibody lacks glycosylation). Glycosylation can be altered to, for example, increase the affinity of the antibody for the antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. Therefore, in one embodiment, the antibodies of the invention are produced by recombinant expression in a cell line which exhibit hypofucosylation pattern, for example, a mammalian cell line with deficient expression of the FUT8 gene encoding fucosyltransferase. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277: 26733-26740). PCT Publication WO 99/54342 by Umana et al. describes cell lines engineered to express glycoprotein-modifying glycosyl transferases (e.g., beta(1,4)—N acetyl-glucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180). Alternatively, the antibodies of the invention can be produced in a yeast or a filamentous fungi engineered for mammalian-like glycosylation pattern, and capable of producing antibodies lacking fucose as glycosylation pattern (see for example EP1297172B1).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Another modification of the antibodies that is contemplated by the invention is a conjugate or a protein fusion of at least the antigen-binding region of the antibody of the invention to serum protein, such as human serum albumin or a fragment thereof to increase half-life of the resulting molecule. Such approach is for example described in Ballance et al. EP0322094.

Another possibility is a fusion of at least the antigen-binding region of the antibody of the invention to proteins capable of binding to serum proteins, such human serum albumin to increase half life of the resulting molecule. Such approach is for example described in Nygren et al., EP 0 486 525.

Methods of Engineering Altered Antibodies

As discussed above, the anti-IL12Rβ1 antibodies having $V_H$ and $V_L$ sequences or full length heavy and light chain sequences shown herein can be used to create new anti-IL12Rβ1 antibodies by modifying full length heavy chain and/or light chain sequences, $V_H$ and/or $V_L$ sequences, or the constant region(s) attached thereto. Thus, in another aspect of the invention, the structural features of an anti-IL12Rβ1 antibody of the invention are used to create structurally related anti-IL12Rβ1 antibodies that retain at least one functional property of the antibodies of the invention, such as binding to human IL12Rβ1 and also inhibiting one or more functional properties of IL12Rβ1 (e.g., inhibiting IL12 and/or IL23 binding to IL12Rβ1, inhibiting IL12 induced IFNγ production in blood cells, etc. . . . ).

For example, one or more CDR regions of the antibodies of the present invention, or mutations thereof, can be combined recombinantly with known framework regions and/or other CDRs to create additional, recombinantly-engineered, anti-IL12Rβ1 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

Accordingly, in another embodiment, the invention provides a method for preparing an anti-IL12Rβ1 antibody consisting of: a heavy chain variable region antibody sequence having a CDR1 sequence selected from the group consisting of SEQ ID NOs: 1-4, a CDR2 sequence selected from the group consisting of SEQ ID NOs: 5-8 and/or a CDR3 sequence selected from the group consisting of SEQ ID NOs: 9-12; and a light chain variable region antibody sequence having a CDR1 sequence selected from the group consisting of SEQ ID NOs: 13-16, a CDR2 sequence selected from the group consisting of SEQ ID NOs: 17-20 and/or a CDR3 sequence selected from the group consisting of SEQ ID NOs: 21-24; altering at least one amino acid residue within the heavy chain variable region antibody sequence and/or the light chain variable region antibody sequence to create at least one altered antibody sequence; and expressing the altered antibody sequence as a protein.

Accordingly, in another embodiment, the invention provides a method for preparing an anti-IL12Rβ1 antibody optimized for expression in a mammalian cell consisting of: a full length heavy chain antibody sequence comprising a variable sequence selected from the group of SEQ ID NOs: 29-32; and a full length light chain antibody sequence comprising a variable sequence selected from the group of 25-28; altering at least one amino acid residue within the full length heavy chain antibody sequence and/or the full length light chain antibody sequence to create at least one altered antibody sequence; and expressing the altered antibody sequence as a protein.

The altered antibody sequence can also be prepared by screening antibody libraries having unique heavy and light CDR3 sequences selected among the group consisting of SEQ ID NO: 9-12 and SEQ ID NO: 21-24 respectively, or minimal essential binding determinants as described in US20050255552, and a diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the anti-IL12Rβ1 antibodies described herein, which functional properties include, but are not limited to, specifically binding to human IL12Rβ1; and/or it inhibits IL12 and IL23 binding to IL12Rβ1 polypeptide; and/or it inhibits IL12 induced IFNγ production in human blood cells; it inhibits IL23 induced IFNγ production in human blood cells; and/or it inhibits IL12 ex vivo IFN-γ production in primate blood cells.

The altered antibody may exhibit one or more, two or more, or three or more of the functional properties discussed above.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-IL12Rβ1 antibody coding sequence and the resulting modified anti-IL12Rβ1 antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Nucleic Acid Molecules Encoding Antibodies of the Invention

Another aspect of the invention pertains to nucleic acid molecules that encode the antibodies of the invention. Examples of variable light chain nucleotide sequences are shown in SEQ ID NOs: 33-36. Examples of variable heavy chain nucleotide sequences are shown in SEQ ID NOs: 37-40. The invention also pertains to nucleic acid molecules that derive from the latter sequences of SEQ ID NOs: 33-40 having been optimized for protein expression in mammalian cells, for example, CHO cell lines.

The nucleic acids may be present in whole cells, in a cell lysate, or may be nucleic acids in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. 1987 Current Protocols in Molecular Biology, Greene Publishing and Wiley Interscience, New York. A nucleic acid of the invention can be, for example, DNA or RNA and may or may not contain intronic sequences. In an embodiment, the nucleic acid is a cDNA molecule. The nucleic acid may be present in a vector such as a phage display vector, or in a recombinant plasmid vector.

Nucleic acids of the invention can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), nucleic acids encoding the antibody can be recovered from various phage clones that are members of the library.

Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to an scFv gene. In these manipulations, a $V_L$- or $V_H$-encoding DNA fragment is operatively linked to another DNA molecule, or to a fragment encoding another protein, such as an antibody constant region or a flexible linker. The term "operatively linked", as used in this context, is intended to mean that the two DNA fragments are joined in a functional manner, for example, such that the amino acid sequences encoded by the two DNA fragments remain in-frame, or such that the protein is expressed under control of a desired promoter.

The isolated DNA encoding the $V_H$ region can be converted to a full-length heavy chain gene by operatively linking the $V_H$-encoding DNA to another DNA molecule encoding heavy chain constant regions (CH1, CH2 and CH3). The sequences of human heavy chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region. In some embodiments, the heavy chain constant region is selected among IgG1 isotypes. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as to a Fab light chain gene) by operatively linking the $V_L$-encoding DNA to another DNA molecule encoding the light chain constant region, CL. The sequences of human light chain constant region genes are known in the art (see e.g., Kabat, E. A., et al., 1991 Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or a lambda constant region.

To create an scFv gene, the $V_H$- and $V_L$-encoding DNA fragments are operatively linked to another fragment encoding a flexible linker, e.g., encoding the amino acid sequence (Gly4-Ser)$_3$, such that the $V_H$ and $V_L$ sequences can be expressed as a contiguous single-chain protein, with the $V_L$ and $V_H$ regions joined by the flexible linker (see e.g., Bird et al., 1988 Science 242:423-426; Huston et at., 1988 Proc. Natl. Acad. Sci. USA 85:5879-5883; McCafferty et al., 1990 Nature 348:552-554).

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Chimeric or humanized antibodies of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101; 5,585,089; 5,693,762 and 6180370 to Queen et al.

In a certain embodiment, the antibodies of the invention are human monoclonal antibodies. Such human monoclonal antibodies directed against IL12Rβ1 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al., 1994 Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGK monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295; Chen, J. at al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97113852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-IL12Rβ1 antibodies of the invention. For example, an alternative transgenic system referred to as the Xenomouse (Abgenix, Inc.) can be used. Such mice are described in, e.g., U.S. Pat. Nos. 5,939,598; 6,075,181; 6,114, 598; 6,150,584 and 6,162,963 to Kucherlapati et al.

Moreover, alternative transchromosomic animal systems expressing human immunoglobulin genes are available in the art and can be used to raise anti-IL12Rβ1 antibodies of the invention. For example, mice carrying both a human heavy chain transchromosome and a human light chain tranchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise anti-IL12Rβ1 antibodies of the invention.

Human recombinant antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Generation of Hybridomas Producing Human Monoclonal Antibodies

To generate hybridomas producing human monoclonal antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3X63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be replated, screened again, and if still positive for human IgG, the monoclonal antibodies can be subcloned at least twice by limiting dilution. The stable subclones can then be cultured in vitro to generate small amounts of antibody in tissue culture medium for characterization.

To purify human monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The monoclonal antibodies can be aliquoted and stored at −80° C.

Generation of Transfectomas Producing Monoclonal Antibodies

Antibodies of the invention also can be produced in a host cell transfectoma using, for example, a combination of recombinant DNA techniques and gene transfection methods as is well known in the art (e.g., Morrison, S. (1985) Science 229:1202).

For example, to express the antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest) and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel (Gene Expression Technology. Methods in Enzymology 185, Academic Press, San Diego, Calif. 1990). It will be appreciated by those skilled in the art that the design of the expression vector, including the selection of regulatory sequences, may depend on such factors as the choice of the host cell to be transformed, the level of expression of protein desired, etc. Regulatory sequences for mammalian host cell expression include viral elements that direct high levels of protein expression in mammalian cells, such as promoters and/or enhancers derived from cytomegalovirus (CMV), Simian Virus 40 (SV40), adenovirus (e.g., the adenovirus major late promoter (AdMLP)), and polyoma. Alternatively, nonviral regulatory sequences may be used, such as the ubiquitin promoter or P-globin promoter. Still further, regulatory elements composed of sequences from different sources, such as the SRa promoter system, which contains sequences from the SV40 early promoter and the long terminal repeat of human T cell leukemia virus type 1 (Takebe, Y. et al., 1988 Mol. Cell. Biol. 8:466-472).

In addition to the antibody chain genes and regulatory sequences, the recombinant expression vectors of the invention may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. It is theoretically possible to express the antibodies of the invention in either prokaryotic or eukaryotic host cells. Expression of antibodies in eukaryotic cells, for example mammalian host cells, yeast or filamentous fungi, is discussed because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R., 1985 Immunology Today 6:12-13).

Mammalian host cells for expressing the recombinant antibodies of the invention include Chinese Hamster Ovary (CHO cells) (including dhfr-CHO cells, described Urlaub and Chasin, 1980 Proc. Natl. Acad. Sci. USA 77:4216-4220 used with a DH FR selectable marker, e.g., as described in R. J. Kaufman and P. A. Sharp, 1982 Mol. Biol. 159:601-621, NSO myeloma cells, COS cells and SP2 cells. In particular, for use with NSO myeloma cells, another expression system is the GS gene expression system shown in WO 87/04462, WO 89/01036 and EP 338,841. In one embodiment, mammalian host cells for expressing the recombinant antibodies of the invention include mammalian cell lines deficient for FUT8 gene expression, for example as described in U.S. Pat. No. 6,946,292B2. When recombinant expression vectors encoding antibody genes are introduced into mammalian host cells, the antibodies are produced by culturing the host cells for a period of time sufficient to allow for expression of the antibody in the host cells or secretion of the antibody into the culture medium in which the host cells are grown. Antibodies can be recovered from the culture medium using standard protein purification methods.

Immunoconjugates

In another aspect, the present invention features an anti-IL12Rβ1 antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D,1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including ZEVALIN (ibritumomab Tiuxetan)™ (DEC Pharmaceuticals) and BEXXAR (tositumomab and iodine I 131 Tositumomab)™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL1"), interleukin-2 ("IL2"), interleukin-6 ("IL6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et at., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific or multispecific molecules comprising an anti-IL12Rβ1 antibody of the invention. An antibody of the invention can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for IL12Rβ1 and a second binding specificity for a second target epitope. For example, the second target epitope is another epitope of IL12Rβ1 different from the first target epitope. Another example is a bispecific molecule comprising at least one first binding specificity for IL12Rβ1 and a second binding specificity for an epitope within IL12Rβ2 or IL23Rα.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778.

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding-specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio) propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

Multivalent Antibodies

In another aspect, the present invention provides multivalent antibodies comprising at least two identical or different antigen-binding portions of the antibodies of the invention binding to IL12Rβ1. In one embodiment, the multivalent antibodies provides at least two, three or four antigen-binding portions of the antibodies. The antigen-binding portions can be linked together via protein fusion or covalent or non covalent linkage. Alternatively, methods of linkage have been described for the bispecific molecules. Tetravalent compounds can be obtained for example by cross-linking antibodies of the antibodies of the invention with an antibody that binds to the constant regions of the antibodies of the invention, for example the Fc or hinge region.

Pharmaceutical Compositions

In another aspect, the present invention provides a composition, e.g., a pharmaceutical composition, containing one or a combination of antibodies of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies that bind to different epitopes on the target antigen or that have complementary activities.

Pharmaceutical compositions of the invention also can be administered in combination therapy, i.e., combined with other agents. For example, the combination therapy can include an anti-IL12Rβ1 antibody of the present invention combined with at least one other anti-inflammatory or another chemotherapeutic agent, for example, an immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). In one embodiment, the carrier should be suitable for subcatuneous route. Depending on the route of administration, the active compound, i.e., antibody, immunoconjugate, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-IL12Rβ1 antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-IL12Rβ1 antibody of the invention can result in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. No. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chemother. 39:180); surfactant protein A receptor (Briscoe et al., 1995 μm. J. Physiol. 1233:134); p120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Immunomethods 4:273.

Uses and Methods of the Invention

The antibodies of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders.

The methods are particularly suitable for treating, preventing or diagnosing IL12Rβ1-related disorders and/or autoimmune and inflammatory disorders, e.g., psoriasis or inflammatory bowel diseases.

The invention also provides methods for decreasing or suppressing IL12 or IL23 induced signaling response in human blood cells by administering a composition comprising a therapeutically efficient dose of the antibodies of the invention.

As used herein, an "IL12Rβ1-related disorder" includes conditions associated with or characterized by aberrant IL12 and/or IL23 levels and/or diseases or conditions that can be treated by reducing or suppressing IL12 and/or IL23 induced signaling response in human blood cells e.g. the production of IFNγ or IL17 as measured in plasma or the extent of phosphorylation of STAT4 protein as measured by flow-cytometric methods or western blot. These include inflammatory conditions and autoimmune diseases, such as rheumatoid arthritis, psoriasis and inflammatory bowel diseases. These further include allergies and allergic conditions, hypersensitivity reactions, and organ or tissue transplant rejection.

For example, the antibodies of the invention may be used for the treatment of recipients of heart, lung, combined heart-lung, liver, kidney, pancreatic, skin or corneal transplants, including allograft rejection or xenograft rejection, and for the prevention of graft-versus-host disease, such as following bone marrow transplant, and organ transplant associated arteriosclerosis.

The antibodies of the invention are useful for the treatment, prevention, or amelioration of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases, including inflammatory conditions and rheumatic diseases involving bone loss, inflammatory pain, spondyloarhropathies including ankolsing spondylitis, Reiter syndrome, reactive arthritis, psoriatic arthritis, and enterophathis arthritis, hypersensitivity (including both airways hypersensitivity and dermal hypersensitivity) and allergies. Specific auto-immune diseases for which antibodies of the invention may be employed include autoimmune haematological disorders (including e.g. hemolytic anaemia, aplastic anaemia, pure red cell anaemia and idiopathic thrombocytopenia), systemic lupus erythematosus, inflammatory muscle disorders, polychondritis, sclerodoma, Wegener granulomatosis, dermatomyositis, chronic active hepatitis, myasthenia gravis, psoriasis, Steven-Johnson syndrome, idiopathic sprue, autoimmune inflammatory bowel disease (including e.g. ulcerative colitis, Crohn's disease and Irritable Bowel Syndrome), endocrine ophthalmopathy, Graves disease, sarcoidosis, multiple sclerosis, primary biliary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy), tumors, multiple sclerosis, inflammatory disease of skin and cornea, myositis, loosening of bone implants, metabolic disorders, such as atherosclerosis, diabetes, and dislipidemia.

The antibodies of the invention are also useful for the treatment, prevention, or amelioration of asthma, bronchitis, pneumoconiosis, pulmonary emphysema, and other obstructive or inflammatory diseases of the airways.

The antibodies of the invention are also useful for treating diseases of bone metabolism including osteoarthritis, osteoporosis and other inflammatory arthritides, and bone loss in general, including age-related bone loss, and in particular periodontal disease.

The antibodies of the invention may be administered as the sole active ingredient or in conjunction with, e.g. as an adjuvant to or in combination to, other drugs e.g. immunosuppressive or immunomodulating agents or other anti-inflammatory agents or other cytotoxic or anti-cancer agents, e.g. for the treatment or prevention of diseases mentioned above. For example, the antibodies of the invention may be used in combination with DMARD, e.g. Gold salts, sulphasalazine, antimalarias, methotrexate, D-penicillamine, azathioprine, mycophenolic acid, cyclosporine A, tacrolimus, sirolimus, minocycline, leflunomide, glococorticoids; a calcineurin inhibitor, e.g. cyclosporin A or FK 506; a modulator of lymphocyte recirculation, e.g. FTY720 and FTY720 analogs; a mTOR inhibitor, e.g. rapamycin, 40-O-(2-hydroxyethyl)-rapamycin, CC1779, ABT578, AP23573 or TAFA-93; an ascomycin having immuno-suppressive properties, e.g. ABT-281, ASM981, etc.; corticosteroids; cyclo-phos-phamide; azathioprene; methotrexate; leflunomide; mizoribine; mycophenolic acid; myco-pheno-late mofetil; 15-deoxyspergualine or an immunosuppressive homologue, analogue or derivative thereof; immunosuppressive monoclonal antibodies, e.g., monoclonal antibodies to leukocyte receptors, e.g., MHC, CD2, CD3, CD4, CD7, CD8, CD25, CD28, CD40. CD45, CD58, CD80, CD86 or their ligands; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM-4 antagonists or VLA-4 antagonists; or a chemotherapeutic agent, e.g. paclitaxel, gemcitabine, cisplatinum, doxorubicin or 5-fluorouracil; anti TNF agents, e.g. monoclonal antibodies to TNF, e.g. infliximab, adalimumab, CDP870, or receptor constructs to TNF-RI or TNF-RII, e.g. Etanercept, PEG-TNF-RI; blockers of proinflammatory cytokines, IL1 blockers, e.g. Anakinra or IL1 trap, AAL160, IL17 blockers, IL13 blockers, IL4 blockers, IL6 blockers; chemokines blockers, e.g inhibitors or activators of proteases, e.g. metalloproteases, anti-IL15 antibodies, anti-IL6 antibodies, anti-IL17 antibodies, anti-IL4 antibodies, anti-IL13 antibodies, anti-CD20 antibodies, anti-Blys or anti-BAFFR antibodies, NSAIDs, such as aspirin or an anti-infectious agent (list not limited to the agent mentioned).

In accordance with the foregoing the present invention provides in a yet further aspect:

A method as defined above comprising co-administration, e.g. concomitantly or in sequence, of a therapeutically effective amount of a IL12Rβ1 antagonist, e.g., an antibody of the invention, and at least one second drug substance, said second drug substance being a immuno-suppressive/immunomodulatory, anti-inflammatory chemotherapeutic or anti-infectious drug, e.g. as indicated above.

Or, a therapeutic combination, e.g. a kit, comprising of a therapeutically effective amount of a) an IL12Rβ1 antagonist, e.g. an antibody of the invention, and b) at least one second substance selected from a immuno-suppressive/immunomodulatory, anti-inflammatory chemotherapeutic or anti-infectious drug, e.g. as indicated above. The kit may comprise instructions for its administration.

Where the antibodies of the invention are administered in conjunction with other immuno-suppressive/immunomodulatory, anti-inflammatory chemotherapeutic or anti-infectious therapy, dosages of the co-administered combination compound will of course vary depending on the type of co-drug employed, e.g. whether it is a DMARD, anti-TNF, IL1 blocker or others, on the specific drug employed, on the condition being treated and so forth. In one specific embodiment, the antibodies of the invention may be administered in combination with anti TNF agents.

In other embodiment, the antibodies of the invention are administered only to patient population which is selected among patients suffering from SLE or RA and exhibiting an abnormal serum level of IL12 respectively IFNγ or IL17 or elevated levels and frequency of phosphoSTAT4 in blood cells. In other embodiment, the antibodies of the invention are administered only to patient population which is selected among group of patients which respond to anti-IL12 or anti-p40 treatment. Biomarkers that identify patients that have an increased likelihood of responding to anti-IL12 (or anti-p40) treatment may be any of the following without being limited to these: elevated levels of serum IL12, elevated levels of certain T cell subsets, mRNA levels of IFNγ, TNFα, IL12Rβ2 or STAT4 from isolated peripheral blood mononuclear cells (PBMCs), phosphoSTAT4 expression in skin biopsies respectively PBMCs.

In one embodiment, the antibodies of the invention can be used to detect levels of IL12Rβ1, or levels of cells that contain IL12Rβ1. This can be achieved, for example, by contacting a sample (such as an in vitro sample) and a control sample with the anti-IL12Rβ1 antibody under conditions that allow for the formation of a complex between the antibody and IL12Rβ1. Any complexes formed between the antibody and IL12Rβ1 are detected and compared in the sample and the control. For example, standard detection methods, well known in the art, such as ELISA and flow cytometric assays, can be performed using the compositions of the invention.

Accordingly, in one aspect, the invention further provides methods for detecting the presence of IL12Rβ1 (e.g., human IL12Rβ1 antigen) in a sample, or measuring the amount of IL12Rβ1, comprising contacting the sample, and a control sample, with an antibody of the invention, or an antigen binding region thereof, which specifically binds to IL12Rβ1, under conditions that allow for formation of a complex between the antibody or portion thereof and IL12Rβ1. The formation of a complex is then detected, wherein a difference in complex formation between the sample compared to the control sample is indicative of the presence of IL12Rβ1 in the sample.

Also within the scope of the invention are kits consisting of the compositions (e.g., antibodies, human antibodies and bispecific molecules) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit. The kit may further comprise tools for diagnosing whether a patient belongs to a group that will response to an anti-IL12Rβ1 antibody treatment, as defined above.

The invention having been fully described, it is further illustrated by the following examples and claims, which are illustrative and are not meant to be further limiting.

EXAMPLES

Methods

1. Screening Assays

The HuCAL® GOLD phagemid library was used for screening antibodies of the invention. The library is based on the HuCAL® concept (Knappik, A. et al. 2000, *J Mol Biol* 296, 57-86) and employs the CysDisplay® technology for displaying Fab antibody fragments on the surface of filamentous phages (Löhning, C. 2001. WO 01/05950). The screening strategy described hereafter can be adapted for other type of libraries and scaffolds, including libraries of non-immunoglobulin scaffolds, thereby allowing to identify IL12Rβ1 binders with similar remarkable properties to the antibodies of the invention but different scaffolds.

1.1 Standard Solid Phase Panning Against IL12Rβ1 on Directly Coated Recombinant Human IL12Rβ1/Fc Fusion Protein For antibody selections, the HuCAL GOLD® antibody-phages were subjected to three rounds of solid phase panning on human recombinant human IL12Rβ1/Fc fusion protein directly coated to MaxiSorp® plates (F96 Nunc-Immunoplate). In detail, 2 wells on a MaxiSorp® plate were coated with 300 μl of 10 μg/ml human IL12Rβ1/Fc fusion protein each o/n at 22° C. The coated wells were washed 2× with 350 μl PBS and blocked with 350 μl 5% MPBS for 2 h at room-temperature (RT) on a microtiter plate shaker. For each panning about $2 \times 10^{13}$ HuCAL GOLD® phage were blocked with equal volume of PBST/5% milk powder (MP) including 1% final concentration of human γ-globulin for 2 h at RT. The coated wells were washed twice with 350 μl PBS after the blocking. 300 μl of pre-blocked HuCAL GOLD® phage were added to each antigen coated well and incubated for 2 h at RT on a shaker. Washing was performed by adding five times 350 μl PBS/0.05% Tween-20 (Sigma, St. Louis, Mo., USA), followed by washing five times with PBS. Elution of phage from the plate was performed with 300 μl 20 mM DTT in 10 mM Tris/HCl pH8 per well for 10 min. The DTT phage eluate was added to 15 ml of *E. coli* TG1, which were grown to an OD600 of 0.6-0.8 at 37° C. in 2xYT medium and incubated in 50 ml plastic tubes for 45 min at 37° C. without shaking for phage infection. Titration of *E. coli* TG1 infected by phages was performed to determine the phage output titer and subsequently centrifugation for 10 min at 5000 rpm was performed. The bacterial pellets were each resuspended in 500 μl 2xYT medium, plated on 2xYT-CG agar plates and incubated o/n at 30° C. Colonies were then scraped off from the plates and phages were rescued and amplified as described above. The second and third round of the solid phase panning on directly coated human IL12Rβ1/Fc fusion protein was performed according to the protocol of the first round except for increasing the stringency of the washing procedures.

1.2 Solid Phase Panning on Captured Via Anti-Human Fc Coated Human IL12R/31/Fc Fusion Protein Same procedure as above described for solid phase panning except coating conditions of the antigen. Here 2.5 μg/ml antigen was captured with 10 μg/ml AffiniPure goat anti human IgG (Fc gamma fragment specific). 2 wells per panning were coated on a MaxiSorp® plate (F96 Nunc-Immunoplate). Phages were blocked additionally with 1% mouse or goat gamma globulins at 1% final concentration (depending on which capture antibody was used, for 1st and 3rd round of panning goat and 2nd round of panning mouse anti human IgG was used) and 1% human gamma globulins final concentration. The capture antibody was blocked for 1 hr at RT with 350 μl of 5% MPBS and subsequently washed twice with PBS before pre-blocked phage mix was added to captured antigen for 2 hrs at RT. All subsequent steps were performed as described above for directly coated antigen.

1.3 Whole Cell Pannings with Ba/F3/IL12Rβ1 Expressing Cells, Including Adsorption Step on Ba/F3 Parental Cells For the antibody selections the HuCAL GOLD® antibody-phages were individually subjected to three rounds of whole cell panning on Ba/F3/IL12Rβ1 expressing cells. In detail, $5 \times 10^6$ to $1 \times 10^7$ cells were pre-blocked with 1 ml 2% PBS/BSA (=blocking buffer) and $5 \times 10^6$ cells each were used per panning. For each panning about $2 \times 10^{13}$ HuCAL GOLD® phage were blocked with equal volume of PBS/4% BSA for 1.5 hrs at 4° C. Pre-blocked HuCAL GOLD® phages were added to pre-blocked target cells and incubated for 2 h at 4° C. on a rotating wheel. Washing was performed three times with 1.5 ml 2% PBS/BSA for 5 min at 4° C. followed by washing once with PBS for 5 min at 4° C. on a rotating wheel. Cells were centrifuged in between 1 min at 2000 rpm at 4° C. Elution of phage was performed by acidic elution with 1 ml of 0.1M glycine, 0.5M NaCl, pH 2.2 at RT for 10 min. To the centrifuged phage eluate 30 µl 2M Tris, unbuffered was added to neutralize the eluate. Subsequently post-adsorption with Ba/F3 parental cells was performed three times with 1E+7 cells per panning eluate for 20 min at 4° C. on a rotating wheel. Cells were centrifuged in between at 2000 rpm for 1 min at 4° C. Used last SN for infection of *E. coli* TG-1 by addition of 9 ml of *E. coli* TG1, which were grown to an OD600 of 0.6-0.8 at 37° C. in 2xYT medium and incubated in 50 ml plastic tubes for 30 min at 37° C. in a waterbath without shaking for phage infection. Titration of infected phages was performed and subsequently centrifugation for 10 min at 5000 rpm was performed, the bacterial pellets were each resuspended in 500 µl 2xYT medium, plated on 2xYT-CG agar plates and incubated o/n at 30° C. Colonies were then scraped off from the plates and phages were rescued and amplified as described above. The second and third round of the whole cell panning with Ba/F3/IL12Rβ1 expressing cells was performed according to the protocol of the first round except for increasing the stringency of the washing procedures.

1.4 Differential Cell Pannings with Ba/F3/IL12Rβ1 Expressing Cells and Recombinant Human IL 12Rβ1/Fc Cell surface expression was checked by FACS analysis with the help of a mouse monoclonal anti-human IL12Rβ1 control antibody (R&D Systems). Panning was performed as above described for whole cell panning for 1st and 3rd round of pannings, including adsorption step on Ba/F3 parental cells during cell panning. 2nd round was performed on directly coated recombinant human IL12Rβ1/Fc fusion protein, as described above for Standard Solid Phase Panning against IL12Rβ1 on directly coated human IL12Rβ1/Fc fusion protein (rh IL12Rβ1).

1.5 Primary Screening for IL12Rβ1-Specific Fabs by ELISA (Direct or Captured Mode)

10 µg/ml of recombinant human IL12Rβ1/Fc fusion protein (R&D Systems) in PBS was coated onto 384 well MaxiSorp® plates o/n at 22° C. for direct screening mode. For screening in captured mode the wells of a 384 well MaxiSorp® plate were coated with 20 µl of 10 µg/ml Affini Pure Goat anti human IgG Fcγ specific in PBS o/n at 4° C. After coating the wells were washed 5× with PBST. Then the wells were blocked with 5% MPBST for 2 hrs at RT. In parallel 15 µl BEL extract was blocked with 15 µl 12.5% MPBST at 22° C. The blocked MaxiSorp® plates were washed 5× with PBST before 20 µl of the blocked BEL extracts was added to the wells and incubated for 2 hrs at RT for the direct screening mode. For captured mode 2.5 µg/ml recombinant human IL12Rβ1/Fc fusion protein (R&D Systems) was added and incubated for 1 hr at RT and subsequently incubated with blocked BEL extracts. For detection of the primary Fab antibodies, the following secondary antibodies were applied: Alkaline phosphatase (AP)-conjugated AffiniPure F(ab')$_2$ fragment, goat anti-human and -anti-mouse or -anti-sheep IgG (Jackson Immuno Research) were added for corresponding control antibodies. For the detection of AP-conjugates the fluorogenic substrate AttoPhos (Roche) was used according to the manufacturer instructions. Between all incubation steps, the wells of the microtiter plate were washed with PBST three times and three times with TBST after the final incubation step with secondary antibody. Fluorescence was measured with a Tecan GENios Pro plate reader.

2. Affinity Determination of Antibodies Identified from Screening Assays 2.1 Affinity Determination using Surface Plasmon Resonance An anti-human-Fc-capture (Dianova) assay was established. Captured Fc-Fusion was used as ligand and Fab was used as analyte.

In detail: CM5 chips (Biacore, Sweden) were coated with 5000-6000 RU anti-Fc (Dianova, Goat anti-Human IgG, Fc Fragment specific; 80 ug/ml in 10 mM acetate buffer, pH 4.5) on all 4 flow cells, using standard EDC-NHS amine coupling chemistry. Flow cells 2 were captured with IL12R1-/Fc fusion (20 µl of 100 nM ligand at a flowrate of 5 µl/ml, 300-400RU). Subsequently the analyte was injected (20 µl, flow rate 20 µl/min) at a concentration range between 15.6 nM to 500 nM. Running conditions: PBS pH7.2. After each cycle, the flow cells were regenerated with 10 mM glycine pH 1.5. The resulting buffer sensogram were manually subtracted from the specific signal for double referencing (buffer injection). All sensograms were plotted and evaluated by using BIA evaluation software 3.1 (Biacore). The summarized affinities of the parental Fab antibodies to human IL12Rβ1 determined by that method were in the range of 2-450 nM.

2.2 Electrochemiluminescene (BioVeris) Based Binding Analysis for Detection of IL12Rβ1 Binding Fab in Bacterial Lysates For the detection of affinity-improved IL12Rβ1-specific antibody fragments in *E. coli* lysates (BEL extracts), binding was analyzed by a BioVeris M-384 SERIES® Workstation. The BioVeris screening was carried out in 96-well polypropylene microtiter plates. BEL extracts were diluted in assay buffer (PBS supplemented with 0.5% BSA and 0.05% Tween-20). Biotinylated IL12Rβ1 was coupled to streptavidin coated paramagnetic beads (M–280, Dynal), according to the manufactures instructions. BEL extract and streptavidin beads coated with biotinylated IL12Rβ1 were incubated o/n at room temperature on a Heidolph-shaker (1000 rpm). For detection, anti-human (Fab)'2 (Dianova) labeled with a ruthenium complex (BV-TAG™) was used.

2.3 Determination of Picomolar Affinities Using Solution Equilibrium Titration (SET)

For $K_D$ determination by solution equilibrium titration (SET), monomer fractions (at least 90% monomer content, analyzed by analytical SEC; Superdex75, Amersham Pharmacia) of Fab protein were used. The applied Fab concentration was similar to or below the expected $K_D$.

Electrochemiluminescence (ECL) based affinity determination in solution and data evaluation were basically performed as described previously (Haenel, C., (2005) et al. *Anal Biochem* 339, 182-184) of recombinant human IL12Rβ1/Fc (1 nM starting concentration) in solution. Biotinylated human IL12Rβ1/Fc coupled to paramagnetic beads (M-280 Streptavidin, Dynal) and rubidium-containing BV-TAG™ (BioVeris Europe) labeled anti-human (Fab)'2 (Dianova) was added and incubated for 30 min. Subsequently, the concentration of unbound Fab was quantified via ECL detection using the M-SERIES® 384 analyzer (BioVeris Europe).

For data evaluation for $K_D$ determination of Fab molecules the following fit model was used (modified according to Abraham et al. *J Mol. Recognit.* 9, 456-461 (1996):

$$y=B\max-(B\max/(2*cFab)*(x+cFab+KD-\mathrm{sqrt}((x+cFab+KD)*(x+cFab+KD)-4*x*cFab)))$$

cFab: applied Fab concentration
cIgG: applied IgG concentration, complete molecule (not binding sites)
x: applied total soluble antigen concentration (binding sites)
sqrt: square root Using the assay conditions described above (monomeric) affinities for the affinity-optimized anti-IL12Rβ1 Fabs were determined in solution.

2.4 IL12Rβ1-IL12/IL23 In Vitro Competitive Binding Inhibition Assay

For the IL12 and IL23 binding inhibition assay, 25 μg recombinant human IL12 and 20 μg IL23 (R&D Systems) were directly coupled (NHS/EDC coupling) to 250 μl carboxylic acid M-270 Dynal magnetic beads (2×10⁹ beads/ml). 50 μl Fab antibodies per well (20 nM stock) in 1:4 dilution steps (Fab concentration: 0.6 pM-10 nM) were incubated for 2 h with 50 μl of 40-100 pM IL12Rβ1/Fc fusion in 96 well plates (Nunc). 25 μl IL12 or IL23 coated beads and 1:500 diluted Streptavidin detection antibody labeled with BV-TAG™ according to instructions of supplier (BioVeris Europe) were added to each well and incubated for 1.5 h. Detection was performed by BioVeris M-384 SERIES® Workstation (BioVeris Europe). EC50 determination was performed by evaluation of the resulting data by a 4-parameter logistic fit model (XLfit, IDBS).

3. In Vitro Characterisation of Antibodies Including Cell-Based Functional Assays 3.1 Inhibition of IL12-Dependent IFNγ Production of Human Blood Cells Peripheral blood mononuclear cells (PBMCs) from donor blood were isolated via Histopaque gradient as described above. Cells were adjusted to 2E+6 cells/ml in X-Vivo 15 medium. 50 μl cells (1E+5) were transferred to a 96 well U bottom plate and incubated with inhibitory antibodies, eg anti human IL12Rβ1Fabs or IgG4 or control mAbs or controls at desired concentrations and pre-incubated for 30 min at RT on a shaker. Stimulation with 2 μg/ml anti-CD3 and anti CD28 mAbs and 2 ng/ml recombinant human cytokine IL12 was performed o/n, for 20 hrs at 37° C. in an 5% CO2 incubator. Next day the supernatant was collected by centrifugation of the cells at 250 g for 5 min at RT and transferred to a fresh 96 well plate and used for ELISA determination or stored at −20° C. until assay was performed.

For the IFNγ ELISA the above collected supernatants were diluted in X-Vivo 15 medium and the ELISA was performed according manufactures protocols BenderMed Systems #BMS228HS or Biozol/Biolegend #BLD-430105. IFNγ production was determined according to IFNγ standard titration curve.

3.2 Inhibition of IL23-Dependent IFNγ Production of Human Blood Cells

Another assay system was investigated, using PHA-stimulated PBMC. In this cell population, the T cells proliferate upon lectin exposure and thus the proportion of T cells in the population increases. In preliminary experiments, the responsiveness of these cells to IL-12, IL-23, IL-18 and LPS, alone or in combination was evaluated and the optimal stimulation conditions were established. The effects of IL-12+IL-18 and IL-23+IL-18 on IFN-γ secretion were induction of around 7 ng/ml and 800 pg/ml, respectively.

3.3 Inhibition of IL12-Dependent IFNγ Production in Whole Blood

Aliquots of 200 μl of anti-coagulated blood were distributed to individual wells of U-bottom 96 well plates (Costar, 3799) where the top and bottom rows were filled with PBS. Compounds were prepared and titrated in X-Vivo 15 medium (Bio-Whitaker, BE04-418F) at 20 fold the desired final concentration and added to triplicate wells per condition (10 μl). The cytokines IL-12 (R&D Systems, 219-IL) and IL-18 (R&D, B001-5) were prepared individually and in combination at 20 fold concentrations and added on top (10 μl), resulting in a total culture volume of 220 μl. Triplicate wells without stimulation or inhibitory compounds were filled with medium only as appropriate.

After 20-24 h of incubation at 37° C., 5% CO2, the plates containing the whole blood were centrifuged at 650 g for 10 minutes and the plasma carefully collected from the top. In order to obtain measurements within the linear range of the standard curve, the plasma was diluted 1:5 with PBS/2 mM EDTA. In cases where the induction was stronger a further determination at higher dilutions 1:10-1:20 was performed.

3.4 Specific Cell Binding of IL12Rβ1 Expressing Ba/F3 Cells Determined by FACS Analysis Cells of the respective cell line (BaF3 cells stable transfected with cyno and human IL12Rβ1; HEK EBNA and Jurkat cells stable transfected with cyno IL12Rβ1) were counted and adjusted to 2×10⁷ cells/ml in PBS/3% FCS/ 0.02% NaN₃ (FACS buffer). FACS staining was performed in V-bottom 96-well microtiter plates (NUNC™, Wiesbaden, Germany) and 1×10⁵ cells per well were mixed with a) purified Fab fragments or b) purified IgG4 or c) positive control antibody (mouse anti IL12Rβ1, R&D Systems, Cat#: MAB839), diluted in FACS buffer and incubated at 4° C. for 1 h. Cells were then washed 2× with 200 μl FACS buffer/well and taken up in 100 μl phycoerythrin-conjugated goat anti-human IgG (H+L) secondary antibody (Jackson ImmunoResearch) which has been diluted 1:200 in FACS buffer. After 45 min incubation at 4° C. cells were washed 3× with FACS buffer, resuspended in 100 μl of FACS buffer and cell surface binding of IL12Rβ1 specific antibodies was measured via FL2 fluorescence intensity of cells in FACSCalibur™ (Becton Dickinson).

4. In Vivo/Ex Vivo Functional Assays 4.1. Cynomolgus Monkey Pharmacodynamics (PD) Assay Heparinized blood samples were distributed in 96-U well plates (190 μl/well). Recombinant human IL-12 (R&D Systems; 100 ng/ml final) and IL-18 (MBL; 50 ng/ml final) were added to each well and the plates were mixed gently for 3 minutes. After an incubation of 24 hrs at 37° C., in 6% $CO_2$, the plates were centrifuged at 2000 rpm for 10 min. The plasma were collected and kept at −80° C. until further processing.

IL-2, TNFα and INFγ were assessed were performed with NHP specific ELISA-kits (CT711, CT148 and CT141), as described by the manufacturer (UcyTech Biosciences, Utrecht).

For the PD readout, the results in pg of INFγ/ml were corrected by the number of lymphocytes found in each sample to be finally expressed as pg/10⁶ lymphocyte.

For the monitoring of circulating IL-2/TNFα/INFγ levels, the results were expressed as pg cytokine/ml.

4.2. Rat In Vivo Compatibility Assay

Rats were injected with defined doses of mAbs and blood samples taken at several intervals to monitor the peak plasma concentration and the rate of elimination to determine the plasma half life time. Since no cross-reactivity to the rat target is expected also no target-related effects (internalization, turnover) can be expected to influence results.

4.3 CD45RBhi Transfer Inflammatory Bowel Disease Mouse Model

To elicit the disease characterized by weight loss CD4+ CD45RBHi T lymphocytes are isolated from BALB/c mouse spleens by FACS-sorting and injected ($2\times10^5$ cells/mouse, i.p.) into 10 week old female SCID mice (day 0). Negative control mice received PBS i.p. and one such mouse is in each cage as a sentinel to monitor possible infections in this immunodeficient colony. Groups of mice receive treatment by subcutaneous injection of mAbs (anti-IL12p40 clone C17.8 or anti-IL12Rβ1 antibody or isotype control) or PBS and d1 7, 14 and 21. The body weight of each mouse is monitored throughout and at the end of the study.

Results

Example 1

Identification of Antagonist Anti-Human IL12Rβ1 Antibody Candidates 1.1 Phage Pannings on Directly Coated IL12Rβ1/Fc The pannings on IL12Rβ1/Fc directly coated on MaxiSorp® resulted in 353 primary hits in the screening on directly coated IL12Rβ1/Fc. Sequence analysis lead to 30 unique Fab sequences. One Fab had several potential N-glycosylation sites in HCDR2, LCDR1 and LCDR2 and was therefore excluded from further analysis.

1.2 Pannings on IL12Rβ1 Captured Via Anti-Fc Antibodies

Panning on IL12Rβ1/Fc captured via goat anti human IgG Fc gamma specific antibodies and subsequent primary screening on IL12Rβ1/Fc captured antigen resulted in 75 primary hits. Sequence analysis revealed 8 unique Fab sequences.

1.3 Whole Cell Pannings on Baf3/IL12Rβ1 Expressing Cells

Whole cell pannings (WCP) comprising 3 selection rounds on Baf3/IL12Rβ1 expressing cells included an adsorption step on Baf3 parental cells. 112 primary hits were identified on directly coated antigen and 122 primary hits were identified on captured antigen. For differential cell panning (DCP), the 1st panning round was on cells, while the 2nd round was on IL12Rβ1/Fc directly coated to MaxiSorp® followed by the 3rd round on cells again. Primary screening of DCP revealed 50 hits on directly coated antigen and 51 hits on captured antigen. In total 14 additional unique Fabs were identified, 11 from WCP and 3 from DCP. 4 Fabs from previous pannings on IL12Rβ1/Fc (direct and capture) were identified again in the cell pannings.

In total 52 Fabs were identified recognizing human IL12Rβ1/Fc in ELISA.

1.4 Characterization of Fabs in ELISA Including Cross-Reactivity to Human IL4Rα/Fc Binding to human IL12Rβ1/Fc and human IL4Rα/Fc was tested in ELISA. 1 and 10 µg/ml of each Fc fusion protein were directly coated on MaxiSorp®, in parallel 1 and 10 µg/ml each were captured via anti-Fc. One Fab showed some cross-reactivity to IL4Rα/Fc in the antigen capture mode, but showed no binding to directly coated IL4Ra/Fc (Data not shown). This Fab was excluded from further analysis. All other tested Fabs showed specific binding to human IL12Rβ1/Fc and no binding to human IL4Rα/Fc on both, directly coated and captured antigen.

1.5 FACS Analysis of Fabs on IL12Rβ1Transfected Baf3 Cells

Binding to human IL12Rβ1/Fc expressed on Baf3 cells was analyzed by FACS. Initially two cell populations of the human IL12Rβ1 transfected cells were detected, having different expression levels of human IL12Rβ1. Two rounds of FACS sorting lead to the detection of a homogenous cell population. 48 of the 52 ELISA positive Fabs showed FACS binding to human IL12Rβ1 transfected BaF3 cells and were subject to further analysis.

1.6 IL12 and IL23 Binding Inhibition Assay (BioVeris) using Fab Antibodies

FACS positive Fabs were analyzed for IL12 and IL23 receptor binding inhibition. 26 Fabs showed IL12/IL12Rβ1 binding inhibition in BioVeris™, while only 14 Fabs showed IL23/IL12Rβ1 binding inhibition in BioVeris™. The different sizes, slightly different binding epitopes or simply different ligand receptor affinities might have caused this discrepancy. Remarkably, IL12 and IL23/IL12Rβ1 binding inhibition in parallel was detectable for 12 Fabs. In general the EC50 values obtained from IL12 inhibition were slightly lower compared to IL23 inhibition (Table 1). One of the 12 Fabs was excluded due to cross reactive binding to rh IL4Ra/Fc in ELISA. Finally the 11 out of 52 Fabs were selected for further evaluation. 3 of the 11 Fabs derived from cell pannings and 8 from pannings on IL12Rβ1/Fc, direct and capture mode. The EC50 values ranged from low nM to several hundred nM (see Table 1).

TABLE 1

IL12 and IL23 receptor binding inhibition in Bioveris.

| MOR# | BIOVeris rhIL-12 IC50 [nM] | BIOVeris rhIL-23 IC50 [nM] |
|---|---|---|
| 4557 | 25 | 83 |
| 4558 | 340 | 240 |
| 4559 | 7 | 11 |
| 4561 | 140 | 214 |
| 4580 | 200 | 620 |
| 4601 | >38 | 1500 |
| 4715 | 760 | 912 |

1.7 Biacore Affinity Determination on Anti-Human Fc-Captured IL12Rβ1/Fc

For the parental Fabs, the affinities were measured on captured IL12Rβ1/Fc in Biacore. The affinity of the 11 preselected Fabs was in the range of 2-450 nM (Table 2).

TABLE 2

Affinities measured by Biacore.

| MOR number | Panning | VH/VL | Biacore KD [nM] |
|---|---|---|---|
| 4557 | IL-12Rβ1/Fc capture and WCP/DCP | H2/λ2 | 34 ± 32 (n = 3) |
| 4558 | IL-12Rβ1/Fc capture | H2/λ3 | 19 ± 13 (n = 2) |
| 4559 | IL-12Rβ1/Fc capture and WCP/DCP | H2/κ1 | 1.7 ± 1.2 (n = 3) |
| 4561 | IL-12Rβ1/Fc capture | H3/λ3 | 453 ± 322 (n = 3) |
| 4576 | IL-12Rβ1/Fc direct | H1A/λ1 | 30 ± 15 (n = 2) |
| 4580 | IL-12Rβ1/Fc direct and WCP/DCP | H3/λ3 | 60 ± 43 (n = 2) |
| 4581 | IL-12Rβ1/Fc direct | H3/λ3 | 71 ± 42 (n = 2) |
| 4601 | IL-12Rβ1/Fc direct | H2/λ1 | 270 (n = 1) |
| 4715 | WCP | H2/λ3 | 80 (n = 1) |
| 4717 | WCP | H3/λ3 | 100 (n = 1) |
| 4724 | DCP | H3/λ3 | 26 (n = 1) |

1.8 IgG4 Conversion of all 11 Pre-Selected Candidates

All 11 pre-selected Fab candidates were converted into IgG4 format. All 11 IgG4 were expressed and purified in ≤1 mg scale. MOR04580 and MOR04581 showed low IgG4 expression level.

1.9 Primary Human T Cells to Determine Antagonistc Potential of anti-IL 12Rβ1 Antibodies Human primary T cells within PBMCs were stimulated with anti-CD3/anti-CD28 to enable IL12 dependent induction of IFN-γ. The selected IgG4 antibodies were tested for dose dependent inhibition of IL12 induced IFN-γ production. The polyclonal positive control anti-IL12Rβ1 antibody AF839 (R&D Systems) inhibited IFN-γ production in a dose-dependent manner, whereas the monoclonal Mab839 did not show clear inhibition. MOR04557, 04559 and 04580 were most active in this assay (Table 3).

Table 3 summarizes the data of antibodies that were selected for affinity maturation.

TABLE 3

Summary data of 7 antibodies selected for maturation.

| MOR# | VH/VL | Biacore $K_D$ [nM] | BIOVeris rhIL-12 IC50 [nM] | BIOVeris rhIL-23 IC50 [nM] | CD3/CD28 IgG4 $IC_{50}$ |
|---|---|---|---|---|---|
| 4557 | H2/λ2 | 34 | 25 | 83 | 1.6 |
| 4558 | H2/λ3 | 19 | 340 | 240 | 4.6 |
| 4559 | H2/κ1 | 1.7 | 7 | 11 | 0.3 |
| 4561 | H2/λ3 | 453 | 140 | 214 | 555 |
| 4580 | H2/λ3 | 60 | 200 | 620 | 1.0 |
| 4601 | H2/λ1 | 270 | >38 | 1500 | 375 |
| 4715 | H2/λ3 | 190 | 760 | 912 | 4.4 |

1.10 Affinity Maturation

The 7 antibodies selected for maturation were grouped in 3 different pools.

Pool 1: MOR04557; MOR04559 (H-CDR2 and L-CDR3 optimization in parallel)

Pool 2: MOR04558; MOR04715 (H-CDR2 and L-CDR3 optimization in parallel)

Pool 3: MOR04561; MOR04580; MOR04601 (H-CDR2 and L-CDR3 in parallel)

1.11 Library Cloning, Phage Preparation and Selection 8 different Fab maturation libraries were cloned and sequencing of randomly picked clones showed a diversity of ~100%. The phage preparation from 8 libraries was partially pooled to finally get 6 phage pools as input for maturation pannings. In total three different maturation strategies were applied to select for the optimized antibodies. For the solution panning on biotinylated human IL-12Rβ1/Fc, reduction of antigen and IL12Rβ1/Fc competition (off-rate selection) were used to increase stringency during selection. As second strategy semi-solution, also called IL12Rβ1/Fc capture panning, was used. Here a reduction of antigen and prolonged washing were performed. Finally a whole cell panning, including a reduction of cell number and prolonged washing were applied. For each selection method, three rounds of maturation pannings were performed.

1.12 Affinity Screening

Affinity screening was performed in BioVeris and 2790 single clones in total, derived from all pannings, were screened for improved affinities on IL12Rβ1/Fc. 264 primary hits coming from all pannings were selected for secondary screening and best hits were sequenced. 32 binders were selected for expression and purification mainly based on the diversity of the H-CDR3.

Example 2

Characterization of Fabs and IgGs of the Invention 2.1 Affinity Determination in SET (BioVeris)

Monomeric affinities for the selected affinity-optimized anti-IL12Rβ1 Fabs were determined in solution, which are summarized in Table 4.

TABLE 4

Affinities of optimized Fab fragments binding to IL12Rβ1 were determined by SET.

| MOR0# | Derivative of Parental | Optimized CDR | SET Affinity $K_D$ [pM] |
|---|---|---|---|
| 5270 | 4557 | H-CDR2 | 57 |
| 5271 | 4557 | H-CDR2 | 21 |
| 5272 | 4559 | L-CDR3 | 140 |
| 5273 | 4715 | H-CDR2 | 89 |
| 5278 | 4561 | H-CDR2 | 31 |
| 5280 | 4559 | L-CDR3 | 41 |
| 5281 | 4559 | L-CDR3 | 1 |
| 5282 | 4559 | L-CDR3 | 14 |
| 5283 | 4559 | L-CDR3 | 16 |
| 5284 | 4559 | L-CDR3 | 25 |
| 5286 | 4558 | L-CDR3 | 59 |
| 5287 | 4558 | L-CDR3 | 110 |
| 5290 | 4561 | L-CDR3 | 360 |
| 5303 | 4559 | L-CDR3 | 23 |
| 5304 | 4558 | L-CDR3 | 350 |
| 5306 | 4561 | L-CDR3 | 1100 |
| 5308 | 4561 | L-CDR3 | 1200 |

Several optimized Fabs showed improvement in affinity up to 700× compared to their parental Fab. SET affinities measured in BioVeris were in the range of 1-1200 pM (Table 4), with most of the affinities in the range of 1-100 pM.

2.2 Cross-Reactivity to IL4Ra/Fc in ELISA

No cross-reactivity to directly coated IL4Ra/Fc was detected in ELISA. In the Fc capture ELISA, most Fabs were specific, but MOR05291 and MOR05292 showed binding to IL4Ra/Fc and CD28/Fc, but these two binders are not pursued for IgG conversion (Data not shown).

2.3 FACS Binding to Human IL12Rβ1 Transfected Baf3 Cells

All optimized Fabs showed good FACS binding to human IL12Rβ1 transfected Baf3 cells (see summary data Table 5)

2.4 Summary Fab Data and Selection for IgG4 Conversion

20 Fabs were selected for IgG4 conversion and expression, including 16 IgG4 directly from maturation and 4 IgG4 from cross-cloning of MOR04561 derivatives (Table 5). The selected IgG4 covered 5 of 7 parental binders and at least one IgG4 from each of the 3 pools was selected to keep a high diversity.

TABLE 5

Summary data

| Clone# | Derivative of Parental | Optimized CDR | SET Affinity $K_D$ [pM] | IL-12 Inhibition $EC_{50}$ [pM] | IL-23 Inhibition $EC_{50}$ [pM] |
|---|---|---|---|---|---|
| 5270 | 4557 | H-CDR2 | 57 | 25 | 130 |
| 5271 | 4557 | H-CDR2 | 21 | 10 | 25 |
| 5272 | 4559 | H-CDR2 | 140 | 4 | 170 |
| 5273 | 4715 | H-CDR2 | 89 | 30 | 1200 |
| 5278 | 4561 | H-CDR2 | 31 | 80 | 240 |
| 5280 | 4559 | L-CDR3 | 41 | 80 | 100 |
| 5281 | 4559 | L-CDR3 | 1 | 60 | 70 |

TABLE 5-continued

Summary data

| Clone# | Derivative of Parental | Optimized CDR | SET Affinity $K_D$ [pM] | IL-12 Inhibition $EC_{50}$ [pM] | IL-23 Inhibition $EC_{50}$ [pM] |
|---|---|---|---|---|---|
| 5282 | 4559 | L-CDR3 | 14 | 90 | 110 |
| 5283 | 4559 | L-CDR3 | 16 | 140 | 100 |
| 5284 | 4559 | L-CDR3 | 25 | 30 | 50 |
| 5286 | 4558 | L-CDR3 | 59 | 90 | 170 |
| 5287 | 4558 | L-CDR3 | 110 | 90 | 60 |
| 5290 | 4561 | L-CDR3 | 360 | 35 | 70 |
| 5303 | 4559 | L-CDR3 | 23 | 30 | 20 |
| 5304 | 4558 | L-CDR3 | 350 | 180 | 100 |
| 5306 | 4561 | L-CDR3 | 1100 | 100 | 100 |
| 5352 | 4561 | 5278(VH) × 5290(VL) | 520 | | |
| 5353 | 4561 | 5278(VH) × 5306(VL) | 830 | | |
| 5354 | 4561 | 5278(VH) × 5308(VL) | 600 | | |
| 5355 | 4561 | 5278(VH) × 5309(VL) | 340 | | |

2.5 IgG4 Conversion of 20 Pre-Selected Candidates

20 IgG4 were converted, expressed and purified. In general the IgGs showed a good expression (Data not shown), but MOR05286 and MOR05287 had to be dialyzed against final buffer PBS pH 6.5, since buffer exchange to standard PBS pH 7.2 resulted in precipitations and significant loss of protein. The isoelectric point of MOR05286 and MOR05287 might have been the reason for the precipitation at pH 7.2. MOR05273 showed a very low expression rate and was therefore excluded from further analysis.

2.6 Characterization of Optimized IgGs

IgG Cross-Reactivity to IL4Ra/Fc in ELISA

All 19 IgG4 showed no cross-reactivity to directly coated IL4Ra/Fc in ELISA, MOR05358 showed no binding to IL12Rβ1 and was excluded from further evaluation (Data not shown).

2.7 FACS Binding of IgGs to Human and Cyno IL12Rβ1Transfected Baf3 Cells

19 IgG4 were analysed for FACS binding to human and cynomolgus IL12Rβ1 transfected Baf3 cells and all showed nearly identical EC50 values on human compared to cynomolgus IL12Rβ1. Differences in maximum binding signal in the saturation phase was most probably due to the known fact that the anti-human Fab detection antibody discriminates between different frameworks (Table 6). The differences between monovalent affinities and the FACS binding EC50 values might result from different conformations or glycoslyation of the receptor antigen. Different avidity effects of the IgGs might also play a role. In addition, cynomolgus IL12Rβ1 was also expressed on human HEK293 and human Jurkat cells (human, peripheral blood, leukemia, T cell). MOR05286 showed clear FACS binding to cynomolgus IL12Rβ1 expressed on human cells. The MFI (mean fluorescent intensity) values are shown in table 7.

TABLE 6

FACS binding EC50 values of IgGs to human and cyno IL12Rβ1 transfected Baf3 cells

| MOR0# | FACS binding to Human IL-12Rβ1 EC50 (n = 3) [pM] | FACS binding to Cyno IL-12Rβ1 EC50 (n = 3) [pM] |
|---|---|---|
| MOR05270 | 118 | 67 |
| MOR05271 | 143 | 73 |
| MOR05272 | 1100 | 1100 |
| MOR05278 | 900 | 931 |
| MOR05280 | 1900 | 1300 |
| MOR05281 | 1200 | 1000 |
| MOR05282 | 1200 | 1000 |
| MOR05283 | 1500 | 1300 |
| MOR05284 | 939 | 922 |
| MOR05286 | 2400 | 4800 |
| MOR05287 | 3500 | 4800 |
| MOR05290 | 64 | 75 |
| MOR05303 | 1200 | 916 |
| MOR05304 | 2300 | 3300 |
| MOR05306 | 68 | 89 |
| MOR05352 | 188 | 136 |
| MOR05353 | 283 | 309 |
| MOR05354 | 244 | 356 |
| MOR05355 | 238 | 425 |
| Mab839 | 2355 | 1474 |

TABLE 7

FACS binding of Fab to cynomolgus IL12Rβ1 expressed on human HEK293, human Jurkat cells and FACS binding of IgG4 to cynomolgus IL12Rβ1 expressed on mouse BaF3 cells. MFI (mean fluorescent intensity) values are listed.

| MOR0# | Derivative of Parental | 7SZP53 Jurkat cyno Mean 1 µg/ml Fab | 2SJU60/61 HEK cyno Mean 1 µg/ml Fab | 3SJU7 BaF3 cyno A+ Mean 1 µg/ml IgG4 |
|---|---|---|---|---|
| 5270 | 4557 | 3 | 2 | 134 |
| 5271 | 4557 | 3 | 2 | 134 |
| 5272 | 4559 | 3 | 2 | 135 |
| 5273 | 4715 | 3 | 3 | not analyzed |
| 5278 | 4561 | 4 | 3 | 350 |
| 5280 | 4559 | 2 | 2 | 141 |
| 5281 | 4559 | 2 | 2 | 144 |
| 5282 | 4559 | 2 | 2 | 185 |
| 5283 | 4559 | 2 | 2 | 140 |
| 5284 | 4559 | 2 | 2 | 133 |
| 5286 | 4558 | 249 | 368 | 271 |
| 5287 | 4558 | 265 | 368 | 278 |
| 5290 | 4561 | 23 | 52 | 86 |
| 5303 | 4559 | 4 | 2 | 150 |
| 5304 | 4558 | 224 | 215 | 287 |
| 5306 | 4561 | 21 | 39 | 93 |

Example 3

Selection of Lead Candidates and Characterization 3.1 Sequences of Lead Candidates Finally 4 lead IgG4 were selected according to their affinity and activity in different bio-assays: MOR05271, MOR05286, MOR05278, MOR05281.

The following table 8 describes SEQ ID numbers for the corresponding CDRs of the selected antibodies of the invention. HCDR1, HCDR2 and HCDR3 stands for the CDR1, CDR2 and CDR3 of the heavy chain of an antibody and LCDR1, LCDR2 and LCDR3 stands for the CDR1, CDR2 and CDR3 of the light chain of an antibody.

TABLE 8

Correspondence mAb# and SEQ IDs

| mAb # | HCDR1 | HCDR2 | HCDR3 | LCDR1 | LCDR2 | LCDR3 |
|---|---|---|---|---|---|---|
| MOR05271 | NO: 1 | NO: 5 | NO: 9 | NO: 13 | NO: 17 | NO: 21 |
| MOR05286 | NO: 2 | NO: 6 | NO: 10 | NO: 14 | NO: 18 | NO: 22 |
| MOR05278 | NO: 3 | NO: 7 | NO: 11 | NO: 15 | NO: 19 | NO: 23 |
| MOR05281 | NO: 4 | NO: 8 | NO: 12 | NO: 16 | NO: 20 | NO: 24 |

3.2 Agonistic Potential of MOR05286 In Vitro

A series of experiments were performed to assess the potential agonistic activity of MOR5286 alone or in the presence of cross-linking reagents. These assays used either monoclonal or polyclonal Abs directed against human IgG constant regions and were directed to monitor activation markers on the surface of T cells as well as cytokine production and proliferation responses.

An agonistic anti-CD28 mAb was used as positive control. This mAb showed a clear induction of activation markers with an average increase of CD25 and CD69 fluorescence intensity of around 10-fold over the control samples and with >80% of human CD4+ T cells expressing CD69 (Data not shown). In contrast, MOR05286 did not induce any general activation response regardless of IL-12+IL-18 stimulation.

In some experiments, a small amount of IFN-γ production was observed following activation of human PBMC with MOR05286 in the presence of the cross-linking mAb anti-IgG4 A (Data not shown). However, this effect was not reproduced in cell cultures which were additionally supplemented with the IFN-γ-inducing cocktail of IL-12+IL-18. Under these conditions, the responses were expectedly rather below that observed by control IgG4. Furthermore, IFN-γ production was not elicited in human whole blood or rhesus PBMC cultures, unstimulated or stimulated with IL-12+IL-18, whereas the inhibitory effects of MOR05286 on cytokine mediated IFN-γ production were consistent in both species. Together these data indicates that MOR05286 does not induce the expression of activation markers on human T cells and does not have the potential to promote cytokine production by human and NHP T cells.

Example 4

Screening Antibodies that Cross-Block IL12Rβ1 Binding Antibodies of the Present Invention 4.1 Biacore Cross-Blocking Assay The following generally describes a suitable Biacore assay for determining whether an antibody or other binding agent cross-blocks or is capable of cross-blocking antibodies according to the invention. It will be appreciated that the assay can be used with any of the IL12Rβ1 binding agents described herein.

The Biacore machine (for example the BIAcore 3000) is operated in line with the manufacturer's recommendations.

IL12Rbeta1 extracellular domain may be coupled to e.g. a CM5 Biacore chip by way of routinely used amine coupling chemistry, e.g. EDC-NHS amine couplilng, to create a IL12Rβ1-coated surface. In order to obtain measurable levels of binding, typically 200-800 resonance units of IL12Rβ1 may be coupled to the chip (this amount gives measurable levels of binding and is at the same time readily saturable by the concentrations of test reagent being used).

An alternative way of attaching IL12Rβ1 to the BIAcore chip is by using a "tagged" version of Il12Rβ1, for example N-terminal or C-terminal His-tagged IL12Rβ1. In this format, an anti-His antibody would be coupled to the Biacore chip and then the His-tagged IL12Rβ1 would be passed over the surface of the chip and captured by the anti-His antibody.

The two antibodies to be assessed for their ability to cross-block each other are mixed in a stoichiometrical amount, e.g. at a one to one molar ratio, of binding sites in a suitable buffer to create the test mixture. The buffer used is typically a buffer which is normally used in protein chemistry, such as e.g. PBS (136 mM NaCl, 2.7 mM KCl, 10 mM $Na_2HPO_4$, 1.76 mM $KH_2PO_4$, pH 7.4). When calculating the concentrations on a binding site-basis the molecular weight of an antibody is assumed to be the total molecular weight of the antibody divided by the number of target (i.e. IL12Rβ1) binding sites on that antibody.

The concentration of each antibody in the test mixture should be high enough to ensure saturation of the binding sites for that antibody on the IL12Rbeta1 molecule which are bound on the BIAcore chip. The antibodies in the mixture are at the same molar concentration (on a binding basis) and that concentration would typically be between 1.0 mM and 1.5 mM (on a binding site basis).

Separate solutions containing the separate antibodies on their own are also prepared. The buffer used for these separate solutions should be the same buffer and at the same concentration as was used for the test mixture.

The test mixture is passed over the IL12Rβ1-coated BIAcore chip and the binding recorded. The bound antibodies are thereafter removed by treating the chip with e.g. an acid, such as 30 mM HCl for about 1 minute. It is important that the IL12Rβ1 molecules which are bound to the chip are not damaged.

The solution of the first antibody alone is then passed over the IL12Rβ1-coated surface and the binding is recorded. Thereafter, the chip is treated to remove all of the bound antibody without damaging the chip-bound IL12Rβ1, e.g. by way of above mentioned acid treatment.

The solution of the second antibody alone is then passed over the IL12Rβ1-coated surface and the amount of binding recorded.

The maximal theoretical binding can be defined as the sum of the binding to IL12Rβ1 of each antibody separately. This is then compared to the actual binding of the mixture of antibodies measured. If the actual binding is lower than that of the theoretical binding, the two antibodies are cross-blocking each other.

4.2 Elisa-Based Cross-Blocking Assay

Cross-blocking of an anti-IL12Rβ1 antibody or another IL12Rβ1 binding agent may also be detected by using an ELISA assay.

The general principle of the ELISA-assay involves coating an anti-IL12Rβ1 antibody onto the wells of an ELISA plate. An excess amount of a second, potentially cross-blocking, anti-IL12Rβ1 antibody is then added in solution (i.e. not bound to the ELISA plate). A limited amount of IL12Rβ1-Fc is then added to the wells.

The antibody which is coated onto the wells and the antibody in solution will compete for binding of the limited number of IL12Rβ1 molecules. The plate is then washed to remove IL12Rβ1-Fc that has not bound to the coated antibody and to also remove the second, solution phase, antibody as well as any complexes formed between the second, solution phase antibody and IL12Rβ1-Fc. The amount of bound IL12Rβ1 is then measured using an appropriate IL12Rβ1 detection reagent. An antibody in solution that is able to cross-block the coated antibody will be able to cause a decrease in the number of IL12Rβ1 molecules that the coated antibody can bind relative to the number of IL12Rβ1 molecules that the coated antibody can bind in the absence of the second, solution phase, antibody.

This assay is described in more detail further below for two antibodies termed Ab-X and Ab-Y. In the instance where Ab-X is chosen to be the immobilized antibody, it is coated onto the wells of the ELISA plate, after which the plates are blocked with a suitable blocking solution to minimize non-specific binding of reagents that are subsequently added. An excess amount of Ab-Y is then added to the ELISA plate such that the moles of Ab-Y IL12Rβ1 binding sites per well are at least 10 fold higher than the moles of Ab-X IL12Rβ1 binding sites that were used, per well, during the coating of the ELISA plate. IL12Rβ1-Fc is then added such that the moles of IL12Rβ1-Fc added per well are at least 25-fold lower than the moles of Ab-X IL12Rβ1 binding sites that were used for coating each well. Following a suitable incubation period, the ELISA plate is washed and a IL12Rβ1 detection reagent is added to measure the amount of IL12Rβ1 specifically bound by the coated anti-IL12Rβ1 antibody (in this case Ab-X). The background signal for the assay is defined as the signal obtained in wells with the coated antibody (in this case Ab-X), second solution phase antibody (in this case Ab-Y), sclerostin buffer only (i.e. no IL12Rβ1) and IL12Rβ1 detection reagents. The positive control signal for the assay is defined as the signal obtained in wells with the coated antibody (in this case Ab-X), second solution phase antibody buffer only (i.e. no second solution phase antibody), IL12Rβ1 and IL12Rβ1 detection reagents. The ELISA assay needs to be run in such a manner so as to have the positive control signal be at least 6 times the background signal.

To avoid any artifacts (e.g. significantly different affinities between Ab-X and Ab-Y for IL12Rβ1) resulting from the choice of which antibody to use as the coating antibody and which to use as the second (competitor) antibody, the cross-blocking assay needs to be run in two formats: 1) format 1 is where Ab-X is the antibody that is coated onto the ELISA plate and Ab-Y is the competitor antibody that is in solution and 2) format 2 is where Ab-Y is the antibody that is coated onto the ELISA plate and Ab-X is the competitor antibody that is in solution.

The invention claimed is:

1. An isolated antibody or an antigen-binding portion of an antibody that binds IL12Rβ1 (SEQ ID NO:41), with a $K_D$ of 100 nM or less and inhibits IL12 and/or IL23 binding to IL12Rβ1 polypeptide as measured in an in vitro competitive binding assay, said antibody further inhibits IL12 dependent INF-γ production in human blood cells with an $IC_{50}$ of 1 nM or less.

2. The antibody according to claim 1, which is a fully human or humanized antibody.

3. The antibody of claim 1, which comprises a mutated or chemically modified amino acid Fc region, wherein said mutated or chemically modified Fc region provides no or decreased ADCC activity when compared with wild type Fc region.

4. The antibody of claim 3, wherein the mutated or chemically modified amino acid Fc region is a silent IgG1 Fc region.

5. The antigen-binding portion according to claim 1, which comprises a pegylated antigen-binding portion of an antibody for IL12Rβ1 polypeptide (SEQ ID NO:41).

6. The antibody or antigen-binding portion according to claim 1, which comprises:
   a) a heavy chain variable region CDR1, CDR2, and CDR3 comprising the sequence of SEQ ID NO: 1, 5, and 9, respectively, and a light chain variable region CDR1, CDR2, and CDR3 comprising the sequence of SEQ ID NO: 13, 17, and 21, respectively;
   b) a heavy chain variable region CDR1, CDR2, and CDR3 comprising the sequence of SEQ ID NO: 2, 6, and 10, respectively, and a light chain variable region CDR1, CDR2, and CDR3 comprising the sequence of SEQ ID NO: 14, 18, and 22, respectively;
   c) a heavy chain variable region CDR1, CDR2, and CDR3 comprising a sequence of SEQ ID NO: 3, 7, and 11, respectively, and a light chain variable region CDR1, CDR2, and CDR3 comprising a sequence of SEQ ID NO: 15, 19, and 23, respectively; or
   d) a heavy chain variable region CDR1, CDR2, and CDR3 comprising a sequence of SEQ ID NO: 4, 8, and 12, respectively, and a light chain variable region CDR1, CDR2, and CDR3 comprising a sequence of SEQ ID NO: 16, 20, and 24, respectively.

7. The antibody, or antigen-binding portion according to claim 1 comprising:
   (a) a heavy chain variable sequence of SEQ ID NO:29 and a light chain variable sequence of SEQ ID NO:25;
   (b) a heavy chain variable sequence of SEQ ID NO:30 and a light chain variable sequence of SEQ ID NO:26;
   (c) a heavy chain variable sequence of SEQ ID NO:31 and a light chain variable sequence of SEQ ID NO:27; or,
   (d) a heavy chain variable sequence of SEQ ID NO:32 and a light chain variable sequence of SEQ ID NO:28.

8. An antibody or antigen binding portion according to claim 6, comprising $V_H$ and $V_L$ sequences having at least 90 percent sequence identity to:
   (a) a heavy chain variable sequence of SEQ ID NO:29 and a light chain variable sequence of SEQ ID NO:25;
   (b) a heavy chain variable sequence of SEQ ID NO:30 and a light chain variable sequence of SEQ ID NO:26;
   (c) a heavy chain variable sequence of SEQ ID NO:31 and a light chain variable sequence of SEQ ID NO:27; or,
   (d) a heavy chain variable sequence of SEQ ID NO:32 and a light chain variable sequence of SEQ ID NO:28.

9. The antibody or antigen-binding portion according to claim 1, which is cross-blocked from binding to IL12Rβ1 (SEQ ID NO:41) by an antibody, or antigen binding fragment thereof, having a heavy chain variable sequence and a light chain variable sequence selected from the group comprising:
   (a) a heavy chain variable sequence of SEQ ID NO:29 and a light chain variable sequence of SEQ ID NO:25;
   (b) a heavy chain variable sequence of SEQ ID NO:30 and a light chain variable sequence of SEQ ID NO:26;
   (c) a heavy chain variable sequence of SEQ ID NO:31 and a light chain variable sequence of SEQ ID NO:27; or,
   (d) a heavy chain variable sequence of SEQ ID NO:32 and a light chain variable sequence of SEQ ID NO:28.

10. A composition comprising an antibody or antigen-binding portion according to claim 1, in combination with a pharmaceutically acceptable excipient, diluent or carrier.

11. An isolated nucleic acid encoding the antibody or antigen-binding portion according to claim 1.

12. A cloning or expression vector comprising one or more nucleic acids according to claim 11.

13. The cloning or expression vector according to claim 12, which comprises at least one nucleic acid selected from the group consisting of any one of SEQ ID NOs: 33-40.

14. A host cell comprising one or more cloning or expression vectors according to claim 12.

15. A process for the production of the antibody or antigen-binding portion of claim 1, comprising culturing a host cell comprising a cloning or expression vector, said cloning or expression vector comprising an isolated nucleic acid encoding said antibody or binding protein and isolating said antibody or binding protein.

\* \* \* \* \*